(12) United States Patent
Stoecker et al.

(10) Patent No.: US 10,393,734 B2
(45) Date of Patent: Aug. 27, 2019

(54) DIAGNOSTIC COINCUBATION ASSAY

(71) Applicant: EUROIMMUN Medizinische Labordiagnostika AG, Luebeck (DE)

(72) Inventors: Winfried Stoecker, Gross Groenau (DE); Bianca Teegen, Rehna (DE); Annika Jahnke, Feldhusen (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 206 days.

(21) Appl. No.: 15/629,528

(22) Filed: Jun. 21, 2017

(65) Prior Publication Data
US 2017/0370911 A1 Dec. 28, 2017

(30) Foreign Application Priority Data
Jun. 21, 2016 (EP) ..................... 16001395

(51) Int. Cl.
*G01N 33/50* (2006.01)
*G01N 33/53* (2006.01)
*G01N 33/543* (2006.01)
*G01N 33/549* (2006.01)
*G01N 33/558* (2006.01)
*G01N 33/567* (2006.01)
*G01N 33/569* (2006.01)
*G01N 33/564* (2006.01)
(Continued)

(52) U.S. Cl.
CPC ............ *G01N 33/5091* (2013.01); *B01L 3/00* (2013.01); *B01L 3/5085* (2013.01); *G01N 1/2813* (2013.01); *G01N 33/5302* (2013.01); *G01N 33/549* (2013.01); *G01N 33/54393* (2013.01); *G01N 33/558* (2013.01); *G01N 33/564* (2013.01); *G01N 33/567* (2013.01); *G01N 33/56966* (2013.01); *B01L 2300/0636* (2013.01); *B01L 2300/0819* (2013.01); *B01L 2300/0822* (2013.01); *B01L 2400/0406* (2013.01); *G01N 2800/06* (2013.01)

(58) Field of Classification Search
None
See application file for complete search history.

(56) References Cited

U.S. PATENT DOCUMENTS

2010/0124750 A1   5/2010  Stöcker et al.
2013/0196336 A1*  8/2013  Hadjivassilliou ..... G01N 33/573
                                                            435/7.1
2016/0320408 A1* 11/2016  Healey ................. G01N 33/505

FOREIGN PATENT DOCUMENTS

EP   2 191 893 A1   6/2010

OTHER PUBLICATIONS

Komorowski et al. (J. Crohn's and Colitis 2013 vol. 7, p. 780-790). (Year: 2013).*

(Continued)

*Primary Examiner* — Changhwa J Cheu
(74) *Attorney, Agent, or Firm* — Grüneberg and Myers PLLC

(57) ABSTRACT

The present invention relates to a method for the diagnosis of a disease comprising contacting a donor tissue section with a liquid capable of extracting an antibody from said donor tissue section and contacting said liquid with an acceptor material comprising an antigen, followed by detection of a complex comprising the antibody and the antigen, and a diagnostically useful carrier comprising a donor tissue section and an acceptor material comprising an antigen.

16 Claims, 5 Drawing Sheets
Specification includes a Sequence Listing.

(a)  (b)  (c)

(51) Int. Cl.
 *B01L 3/00* (2006.01)
 *G01N 1/28* (2006.01)

(56) References Cited

OTHER PUBLICATIONS

Chardes et al. (Immunogenetics 2002 vol. 54, p. 141-157) (Year: 2002).*
Herbert et al. (Ann Rheum. Dis. 2016 vol. 75, p. 696-701). (Year: 2016).*
U.S. Appl. No. 15/032,193, filed Apr. 26, 2016, US 2016-0258971 A1, Winfried Stoecker.
U.S. Appl. No. 12/622,279, filed Nov. 19, 2009, US 2010-0124750 A1, Winfried Stoöcker, et al.
Extended European Search Report dated Sep. 27, 2016 in Patent Application No. 16001395.9.
J. A. Snook, et al., "Serum and tissue autoantibodies to colonic epithelium in ulcerative colitis", Gut, XP055301786, vol. 32, No. 2, Feb. 1, 1991, pp. 163-166.
Misa Hirose, et al., "Enzymatic autoantibody glycan hydrolysis alleviates autoimmunity against type VII collagen", Elsevier, Journal of Autoimmunity, XP055301577, vol. 39, No. 4, Dec. 1, 2012, pp. 304-314.
Raghu Kalluri, et al., "Specificity of Circulating and Tissue-Bound Autoantibodies in Goodpasture Syndrome", Proceedings of the Association of American Physicians, XP009191610, vol. 108, No. 2, Mar. 1, 1996, pp. 134-139.

\* cited by examiner

SEQUENCE LISTING

```
<160> NUMBER OF SEQ ID NOS: 18

<210> SEQ ID NO 1
<211> LENGTH: 17
<212> TYPE: PRT
<213> ORGANISM: Artificial Sequence
<220> FEATURE:
<223> OTHER INFORMATION: SEQ ID NO 1 artificial antigen

<400> SEQUENCE: 1

Pro Leu Gln Pro Glu Gln Pro Phe Pro Glu Gln Leu Pro Gln Phe Glu
1               5                   10                  15

Glu

<210> SEQ ID NO 2
<211> LENGTH: 65
<212> TYPE: PRT
<213> ORGANISM: Artificial Sequence
<220> FEATURE:
<223> OTHER INFORMATION: SEQ ID NO 2 artificial antigen

<400> SEQUENCE: 2

Met Ala His Met Pro Leu Gln Pro Glu Gln Pro Phe Pro Glu Gln Leu
1               5                   10                  15

Pro Gln Phe Glu Glu Met Pro Leu Gln Pro Glu Gln Pro Phe Pro Glu
            20                  25                  30

Gln Leu Pro Gln Phe Glu Glu Met Pro Leu Gln Pro Glu Gln Pro Phe
        35                  40                  45

Pro Glu Gln Leu Pro Gln Phe Glu Glu Met Val His His His His His
    50                  55                  60

His
65
```

```
<210> SEQ ID NO 3
<211> LENGTH: 9
<212> TYPE: PRT
<213> ORGANISM: Artificial Sequence
<220> FEATURE:
<223> OTHER INFORMATION: SEQ ID NO 3 artificial epitope

<400> SEQUENCE: 3

Gln Leu Trp Glu Ile Pro Glu Gln Ser
1               5

<210> SEQ ID NO 4
<211> LENGTH: 16
<212> TYPE: PRT
<213> ORGANISM: Artificial Sequence
<220> FEATURE:
<223> OTHER INFORMATION: SEQ ID NO 4 artificial antigen

<400> SEQUENCE: 4

Gln Pro Glu Gln Pro Gln Gln Ser Phe Pro Glu Gln Glu Arg Pro Phe
1               5                   10                  15

<210> SEQ ID NO 5
<211> LENGTH: 6
<212> TYPE: PRT
<213> ORGANISM: Artificial Sequence
<220> FEATURE:
<223> OTHER INFORMATION: SEQ ID NO 5 artificial antigen
<220> FEATURE:
<221> NAME/KEY: VARIANT
<222> LOCATION: (2)..(2)
<223> OTHER INFORMATION: Xaa can be any naturally occurring amino acid

<400> SEQUENCE: 5

Gln Xaa Gln Pro Phe Pro
1               5

<210> SEQ ID NO 6
<211> LENGTH: 73
<212> TYPE: PRT
<213> ORGANISM: Artificial Sequence
<220> FEATURE:
<223> OTHER INFORMATION: SEQ ID NO 6 artificial antigen

<400> SEQUENCE: 6

Glu Glu Val Arg Lys Leu Lys Ala Arg Val Asp Glu Leu Glu Arg Ile
1               5                   10                  15

Arg Arg Ser Ile Leu Pro Tyr Gly Asp Ser Met Asp Arg Ile Glu Lys
            20                  25                  30

Asp Arg Leu Gln Gly Met Ala Pro Ala Ala Gly Ala Asp Leu Asp Lys
        35                  40                  45

Ile Gly Leu His Ser Asp Ser Gln Glu Glu Leu Trp Met Phe Val Arg
    50                  55                  60

Lys Lys Leu Met Met Glu Gln Glu Asn
65                  70

<210> SEQ ID NO 7
<211> LENGTH: 312
<212> TYPE: PRT
<213> ORGANISM: Artificial Sequence
<220> FEATURE:
<223> OTHER INFORMATION: SEQ ID NO 7 artificial antigen
```

<400> SEQUENCE: 7

Met Ser His His His His His His Ser Met Glu Glu Val Arg
1               5                   10                  15

Lys Leu Lys Ala Arg Val Asp Glu Leu Glu Arg Ile Arg Ser Ile
            20                  25                  30

Leu Pro Tyr Gly Asp Ser Met Asp Arg Ile Glu Lys Asp Arg Leu Gln
            35                  40                  45

Gly Met Ala Pro Ala Ala Gly Ala Asp Leu Asp Lys Ile Gly Leu His
    50                  55                  60

Ser Asp Ser Gln Glu Glu Leu Trp Met Phe Val Arg Lys Lys Leu Met
65                  70                  75                  80

Met Glu Gln Glu Asn Gly Thr Glu Glu Val Arg Lys Leu Lys Ala Arg
                85                  90                  95

Val Asp Glu Leu Glu Arg Ile Arg Arg Ser Ile Leu Pro Tyr Gly Asp
            100                 105                 110

Ser Met Asp Arg Ile Glu Lys Asp Arg Leu Gln Gly Met Ala Pro Ala
            115                 120                 125

Ala Gly Ala Asp Leu Asp Lys Ile Gly Leu His Ser Asp Ser Gln Glu
    130                 135                 140

Glu Leu Trp Met Phe Val Arg Lys Lys Leu Met Met Glu Gln Glu Asn
145                 150                 155                 160

Lys Leu Glu Glu Val Arg Lys Leu Lys Ala Arg Val Asp Glu Leu Glu
                165                 170                 175

Arg Ile Arg Arg Ser Ile Leu Pro Tyr Gly Asp Ser Met Asp Arg Ile
            180                 185                 190

Glu Lys Asp Arg Leu Gln Gly Met Ala Pro Ala Ala Gly Ala Asp Leu
            195                 200                 205

Asp Lys Ile Gly Leu His Ser Asp Ser Gln Glu Glu Leu Trp Met Phe
    210                 215                 220

Val Arg Lys Lys Leu Met Met Glu Gln Glu Asn Gly Ser Glu Glu Val
225                 230                 235                 240

Arg Lys Leu Lys Ala Arg Val Asp Glu Leu Glu Arg Ile Arg Arg Ser
                245                 250                 255

Ile Leu Pro Tyr Gly Asp Ser Met Asp Arg Ile Glu Lys Asp Arg Leu
            260                 265                 270

Gln Gly Met Ala Pro Ala Ala Gly Ala Asp Leu Asp Lys Ile Gly Leu
            275                 280                 285

His Ser Asp Ser Gln Glu Glu Leu Trp Met Phe Val Arg Lys Lys Leu
    290                 295                 300

Met Met Glu Gln Glu Asn Leu Glu
305                 310

<210> SEQ ID NO 8
<211> LENGTH: 779
<212> TYPE: PRT
<213> ORGANISM: Artificial Sequence
<220> FEATURE:
<223> OTHER INFORMATION: SEQ ID NO 8 artificial antigen

<400> SEQUENCE: 8

Met Asp Cys Thr Phe Lys Pro Asp Phe Glu Met Thr Val Lys Glu Cys
1               5                   10                  15

Gln His Ser Gly Glu Leu Ser Ser Arg Asn Thr Gly His Leu His Pro
            20                  25                  30

```
Thr Pro Arg Ser Pro Leu Leu Arg Trp Thr Gln Glu Pro Gln Pro Leu
         35                  40                  45
Glu Glu Lys Trp Gln His Arg Val Val Glu Gln Ile Pro Lys Glu Val
 50                  55                  60
Gln Phe Gln Pro Pro Gly Ala Pro Leu Glu Lys Glu Lys Ser Gln Gln
 65                  70                  75                  80
Cys Tyr Ser Glu Tyr Phe Ser Gln Thr Ser Thr Glu Leu Gln Ile Thr
                 85                  90                  95
Phe Asp Glu Thr Asn Pro Ile Thr Arg Leu Ser Glu Ile Glu Lys Ile
             100                 105                 110
Arg Asp Gln Ala Leu Asn Asn Ser Arg Pro Pro Val Arg Tyr Gln Asp
         115                 120                 125
Asn Ala Cys Glu Met Glu Leu Val Lys Val Leu Thr Pro Leu Glu Ile
     130                 135                 140
Ala Lys Asn Lys Gln Tyr Asp Met His Thr Glu Val Thr Thr Leu Lys
145                 150                 155                 160
Gln Glu Lys Asn Pro Val Pro Ser Ala Glu Glu Trp Met Leu Glu Gly
                 165                 170                 175
Cys Arg Ala Ser Gly Gly Leu Lys Lys Gly Asp Phe Leu Lys Lys Gly
             180                 185                 190
Leu Glu Pro Glu Thr Phe Gln Asn Phe Asp Gly Asp His Ala Cys Ser
         195                 200                 205
Val Arg Asp Asp Glu Phe Lys Phe Gln Gly Leu Arg His Thr Val Thr
     210                 215                 220
Ala Arg Gln Leu Val Glu Ala Lys Leu Leu Asp Met Arg Thr Ile Glu
225                 230                 235                 240
Gln Leu Arg Leu Gly Leu Lys Thr Val Glu Glu Val Gln Lys Thr Leu
                 245                 250                 255
Asn Lys Phe Leu Thr Lys Ala Thr Ser Ile Ala Gly Leu Tyr Leu Glu
             260                 265                 270
Ser Thr Lys Glu Lys Ile Ser Phe Ala Ser Ala Ala Glu Arg Ile Ile
         275                 280                 285
Ile Asp Lys Met Val Ala Leu Ala Phe Leu Glu Ala Gln Ala Ala Thr
     290                 295                 300
Gly Phe Ile Ile Asp Pro Ile Ser Gly Gln Thr Tyr Ser Val Glu Asp
305                 310                 315                 320
Ala Val Leu Lys Gly Val Val Asp Pro Glu Phe Arg Ile Arg Leu Leu
                 325                 330                 335
Glu Ala Glu Lys Ala Ala Val Gly Tyr Ser Tyr Ser Ser Lys Thr Leu
             340                 345                 350
Ser Val Phe Gln Ala Met Glu Asn Arg Met Leu Asp Arg Gln Lys Gly
         355                 360                 365
Lys His Ile Leu Glu Ala Gln Ile Ala Ser Gly Gly Val Ile Asp Pro
     370                 375                 380
Val Arg Gly Ile Arg Val Pro Pro Glu Ile Ala Leu Gln Gln Gly Leu
385                 390                 395                 400
Leu Asn Asn Ala Ile Leu Gln Phe Leu His Glu Pro Ser Ser Asn Thr
                 405                 410                 415
Arg Val Phe Pro Asn Pro Asn Asn Lys Gln Ala Leu Tyr Tyr Ser Glu
             420                 425                 430
Leu Leu Arg Met Cys Val Phe Asp Val Glu Ser Gln Cys Phe Leu Phe
         435                 440                 445
```

```
Pro Phe Gly Glu Arg Asn Ile Ser Asn Leu Asn Val Lys Lys Thr His
    450                 455                 460

Arg Ile Ser Val Val Asp Thr Lys Thr Gly Ser Glu Leu Thr Val Tyr
465                 470                 475                 480

Glu Ala Phe Gln Arg Asn Leu Ile Glu Lys Ser Ile Tyr Leu Glu Leu
                485                 490                 495

Ser Gly Gln Gln Tyr Gln Trp Lys Glu Ala Met Phe Phe Glu Ser Tyr
            500                 505                 510

Gly His Ser Ser His Met Leu Thr Asp Thr Lys Thr Gly Leu His Phe
        515                 520                 525

Asn Ile Asn Glu Ala Ile Glu Gln Gly Thr Ile Asp Lys Ala Leu Val
530                 535                 540

Lys Lys Tyr Gln Glu Gly Leu Ile Thr Leu Thr Glu Leu Ala Asp Ser
545                 550                 555                 560

Leu Leu Ser Arg Leu Val Pro Lys Lys Asp Leu His Ser Pro Val Ala
                565                 570                 575

Gly Tyr Trp Leu Thr Ala Ser Gly Glu Arg Ile Ser Val Leu Lys Ala
            580                 585                 590

Ser Arg Arg Asn Leu Val Asp Arg Ile Thr Ala Leu Arg Cys Leu Glu
            595                 600                 605

Ala Gln Val Ser Thr Gly Gly Ile Ile Asp Pro Leu Thr Gly Lys Lys
610                 615                 620

Tyr Arg Val Ala Glu Ala Leu His Arg Gly Leu Val Asp Glu Gly Phe
625                 630                 635                 640

Ala Gln Gln Leu Arg Gln Cys Glu Leu Val Ile Thr Gly Ile Gly His
                645                 650                 655

Pro Ile Thr Asn Lys Met Met Ser Val Val Glu Ala Val Asn Ala Asn
            660                 665                 670

Ile Ile Asn Lys Glu Met Gly Ile Arg Cys Leu Glu Phe Gln Tyr Leu
        675                 680                 685

Thr Gly Gly Leu Ile Glu Pro Gln Val His Ser Arg Leu Ser Ile Glu
        690                 695                 700

Glu Ala Leu Gln Val Gly Ile Ile Asp Val Leu Ile Ala Thr Lys Leu
705                 710                 715                 720

Lys Asp Gln Lys Ser Tyr Val Arg Asn Ile Ile Cys Pro Gln Thr Lys
                725                 730                 735

Arg Lys Leu Thr Tyr Lys Glu Leu Glu Lys Ala Asp Phe Asp Phe
            740                 745                 750

His Thr Gly Leu Lys Leu Leu Glu Val Ser Glu Pro Leu Met Thr Gly
        755                 760                 765

Ile Ser Ser Leu Tyr Tyr Ser Ser Leu Leu Glu
770                 775

<210> SEQ ID NO 9
<211> LENGTH: 1463
<212> TYPE: PRT
<213> ORGANISM: Artificial Sequence
<220> FEATURE:
<223> OTHER INFORMATION: SEQ ID NO 9 artificial antigen

<400> SEQUENCE: 9

Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30
```

```
Leu Glu Trp Gln Asp Lys Gly Ile Phe Val Ile Gln Ser Glu Ser Leu
             35                  40                  45

Lys Lys Cys Ile Gln Ala Gly Lys Ser Val Leu Thr Leu Glu Asn Cys
 50                  55                  60

Lys Gln Ala Asn Lys His Met Leu Trp Lys Trp Val Ser Asn His Gly
 65                  70                  75                  80

Leu Phe Asn Ile Gly Gly Ser Gly Cys Leu Gly Leu Asn Phe Ser Ala
                 85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
            115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
    195                 200                 205

Arg Tyr Glu Arg Asp Glu Lys Trp Gly Phe Cys Pro Asp Pro Thr Ser
    210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
    275                 280                 285

Glu Val Trp Met Gly Leu Asn Gln Leu Asp Glu His Ala Gly Trp Gln
    290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu Ile Val Glu Lys
    355                 360                 365

Asp Ala Trp Lys Tyr Tyr Ala Thr His Cys Glu Pro Gly Trp Asn Pro
    370                 375                 380

Tyr Asn Arg Asn Cys Tyr Lys Leu Gln Lys Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
    435                 440                 445
```

-continued

```
Ser Phe Glu Trp Ser Asn Asp Ser Ser Val Ile Phe Thr Asn Trp His
    450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Arg
            485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
            515                 520                 525

Ile Asp Thr Val Leu Arg Ser Phe Asp Gln Ala Ser Ser Gly Tyr Tyr
    530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
    595                 600                 605

His Gln Pro Arg Tyr Ser Gly Gly Cys Val Ala Met Arg Gly Arg His
    610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg Trp Pro Phe His Pro Cys Tyr Leu Asp Trp Glu Ser Glu Pro
            660                 665                 670

Gly Leu Ala Ser Cys Phe Lys Val Phe His Ser Glu Lys Val Leu Met
            675                 680                 685

Lys Arg Thr Trp Arg Glu Ala Glu Ala Phe Cys Glu Glu Phe Gly Ala
690                 695                 700

His Leu Ala Ser Phe Ala His Ile Glu Glu Asn Phe Val Asn Glu
705                 710                 715                 720

Leu Leu His Ser Lys Phe Asn Trp Thr Glu Glu Arg Gln Phe Trp Ile
                725                 730                 735

Gly Phe Asn Lys Arg Asn Pro Leu Asn Ala Gly Ser Trp Glu Trp Ser
            740                 745                 750

Asp Arg Thr Pro Val Val Ser Ser Phe Leu Asp Asn Thr Tyr Phe Gly
    755                 760                 765

Glu Asp Ala Arg Asn Cys Ala Val Tyr Lys Ala Asn Lys Thr Leu Leu
            770                 775                 780

Pro Leu His Cys Gly Ser Lys Arg Glu Trp Ile Cys Lys Ile Pro Arg
785                 790                 795                 800

Asp Val Lys Pro Lys Ile Pro Phe Trp Tyr Gln Tyr Asp Val Pro Trp
                805                 810                 815

Leu Phe Tyr Gln Asp Ala Glu Tyr Leu Phe His Thr Phe Ala Ser Glu
            820                 825                 830

Trp Leu Asn Phe Glu Phe Val Cys Ser Trp Leu His Ser Asp Leu Leu
            835                 840                 845

Thr Ile His Ser Ala His Glu Gln Glu Phe Ile His Ser Lys Ile Lys
    850                 855                 860
```

```
Ala Leu Ser Lys Tyr Gly Ala Ser Trp Trp Ile Gly Leu Gln Glu
865                 870                 875                 880

Arg Ala Asn Asp Glu Phe Arg Trp Arg Asp Gly Thr Pro Val Ile Tyr
            885                 890                 895

Gln Asn Trp Asp Thr Gly Arg Glu Arg Thr Val Asn Asn Gln Ser Gln
            900                 905                 910

Arg Cys Gly Phe Ile Ser Ser Ile Thr Gly Leu Trp Gly Ser Glu Glu
            915                 920                 925

Cys Ser Val Ser Met Pro Ser Ile Cys Lys Arg Lys Val Trp Leu
930                 935                 940

Ile Glu Lys Lys Lys Asp Thr Pro Lys Gln His Gly Thr Cys Pro Lys
945                 950                 955                 960

Gly Trp Leu Tyr Phe Asn Tyr Lys Cys Leu Leu Leu Asn Ile Pro Lys
            965                 970                 975

Asp Pro Ser Ser Trp Lys Asn Trp Thr His Ala Gln His Phe Cys Ala
            980                 985                 990

Glu Glu Gly Gly Thr Leu Val Ala  Ile Glu Ser Glu Val  Glu Gln Ala
            995                 1000                1005

Phe Ile  Thr Met Asn Leu Phe  Gly Gln Thr Thr Ser  Val Trp Ile
1010                1015                1020

Gly Leu  Gln Asn Asp Asp Tyr  Glu Thr Trp Leu Asn  Gly Lys Pro
1025                1030                1035

Val Val  Tyr Ser Asn Trp Ser  Pro Phe Asp Ile Ile  Asn Ile Pro
1040                1045                1050

Ser His  Asn Thr Thr Glu Val  Gln Lys His Ile Pro  Leu Cys Ala
1055                1060                1065

Leu Leu  Ser Ser Asn Pro Asn  Phe His Phe Thr Gly  Lys Trp Tyr
1070                1075                1080

Phe Glu  Asp Cys Gly Lys Glu  Gly Tyr Gly Phe Val  Cys Glu Lys
1085                1090                1095

Met Gln  Asp Thr Ser Gly His  Gly Val Asn Thr Ser  Asp Met Tyr
1100                1105                1110

Pro Met  Pro Asn Thr Leu Glu  Tyr Gly Asn Arg Thr  Tyr Lys Ile
1115                1120                1125

Ile Asn  Ala Asn Met Thr Trp  Tyr Ala Ala Ile Lys  Thr Cys Leu
1130                1135                1140

Met His  Lys Ala Gln Leu Val  Ser Ile Thr Asp Gln  Tyr His Gln
1145                1150                1155

Ser Phe  Leu Thr Val Val Leu  Asn Arg Leu Gly Tyr  Ala His Trp
1160                1165                1170

Ile Gly  Leu Phe Thr Thr Asp  Asn Gly Leu Asn Phe  Asp Trp Ser
1175                1180                1185

Asp Gly  Thr Lys Ser Ser Phe  Thr Phe Trp Lys Asp  Glu Glu Ser
1190                1195                1200

Ser Leu  Leu Gly Asp Cys Val  Phe Ala Asp Ser Asn  Gly Arg Trp
1205                1210                1215

His Ser  Thr Ala Cys Glu Ser  Phe Leu Gln Gly Ala  Ile Cys His
1220                1225                1230

Val Pro  Pro Glu Thr Arg Gln  Ser Glu His Pro Glu  Leu Cys Ser
1235                1240                1245

Glu Thr  Ser Ile Pro Trp Ile  Lys Phe Lys Ser Asn  Cys Tyr Ser
1250                1255                1260
```

```
Phe Ser Thr Val Leu Asp Ser Met Ser Phe Glu Ala Ala His Glu
    1265                1270                1275

Phe Cys Lys Lys Glu Gly Ser Asn Leu Leu Thr Ile Lys Asp Glu
1280                1285                1290

Ala Glu Asn Ala Phe Leu Leu Glu Glu Leu Phe Ala Phe Gly Ser
    1295                1300                1305

Ser Val Gln Met Val Trp Leu Asn Ala Gln Phe Asp Gly Asn Asn
    1310                1315                1320

Glu Thr Ile Lys Trp Phe Asp Gly Thr Pro Thr Asp Gln Ser Asn
    1325                1330                1335

Trp Gly Ile Arg Lys Pro Asp Thr Asp Tyr Phe Lys Pro His His
    1340                1345                1350

Cys Val Ala Leu Arg Ile Pro Glu Gly Leu Trp Gln Leu Ser Pro
    1355                1360                1365

Cys Gln Glu Lys Lys Gly Phe Ile Cys Lys Met Glu Ala Asp Ile
    1370                1375                1380

His Thr Ala Glu Ala Leu Pro Glu Lys Gly Pro Ser His Ser Ile
    1385                1390                1395

Ile Pro Leu Ala Val Val Leu Thr Leu Ile Val Ile Val Ala Ile
    1400                1405                1410

Cys Thr Leu Ser Phe Cys Ile Tyr Lys His Asn Gly Gly Phe Phe
    1415                1420                1425

Arg Arg Leu Ala Gly Phe Arg Asn Pro Tyr Tyr Pro Ala Thr Asn
    1430                1435                1440

Phe Ser Thr Val Tyr Leu Glu Glu Asn Ile Leu Ile Ser Asp Leu
    1445                1450                1455

Glu Lys Ser Asp Gln
    1460

<210> SEQ ID NO 10
<211> LENGTH: 1657
<212> TYPE: PRT
<213> ORGANISM: Artificial Sequence
<220> FEATURE:
<223> OTHER INFORMATION: SEQ ID NO 10 artificial antigen

<400> SEQUENCE: 10

Met Gly Leu Gln Ala Arg Arg Trp Ala Ser Gly Ser Arg Gly Ala Ala
1               5                   10                  15

Gly Pro Arg Arg Gly Val Leu Gln Leu Leu Pro Leu Pro Leu Pro Leu
            20                  25                  30

Pro Leu Leu Leu Leu Leu Leu Arg Pro Gly Ala Gly Arg Ala Ala
        35                  40                  45

Ala Gln Gly Glu Ala Glu Ala Pro Thr Leu Tyr Leu Trp Lys Thr Gly
    50                  55                  60

Pro Trp Gly Arg Cys Met Gly Asp Glu Cys Gly Pro Gly Gly Ile Gln
65                  70                  75                  80

Thr Arg Ala Val Trp Cys Ala His Val Glu Gly Trp Thr Thr Leu His
                85                  90                  95

Thr Asn Cys Lys Gln Ala Glu Arg Pro Asn Asn Gln Asn Cys Phe
            100                 105                 110

Lys Val Cys Asp Trp His Lys Glu Leu Tyr Asp Trp Arg Leu Gly Pro
        115                 120                 125

Trp Asn Gln Cys Gln Pro Val Ile Ser Lys Ser Leu Glu Lys Pro Leu
    130                 135                 140
```

```
Glu Cys Ile Lys Gly Glu Gly Ile Gln Val Arg Glu Ile Ala Cys
145                 150                 155                 160

Ile Gln Lys Asp Lys Asp Ile Pro Ala Glu Asp Ile Ile Cys Glu Tyr
            165                 170                 175

Phe Glu Pro Lys Pro Leu Leu Glu Gln Ala Cys Leu Ile Pro Cys Gln
                180                 185                 190

Gln Asp Cys Ile Val Ser Glu Phe Ser Ala Trp Ser Glu Cys Ser Lys
            195                 200                 205

Thr Cys Gly Ser Gly Leu Gln His Arg Thr Arg His Val Val Ala Pro
210                 215                 220

Pro Gln Phe Gly Gly Ser Gly Cys Pro Asn Leu Thr Glu Phe Gln Val
225                 230                 235                 240

Cys Gln Ser Ser Pro Cys Glu Ala Glu Glu Leu Arg Tyr Ser Leu His
                245                 250                 255

Val Gly Pro Trp Ser Thr Cys Ser Met Pro His Ser Arg Gln Val Arg
                260                 265                 270

Gln Ala Arg Arg Arg Gly Lys Asn Lys Glu Arg Glu Lys Asp Arg Ser
            275                 280                 285

Lys Gly Val Lys Asp Pro Glu Ala Arg Glu Leu Ile Lys Lys Lys Arg
290                 295                 300

Asn Arg Asn Arg Gln Asn Arg Gln Glu Asn Lys Tyr Trp Asp Ile Gln
305                 310                 315                 320

Ile Gly Tyr Gln Thr Arg Glu Val Met Cys Ile Asn Lys Thr Gly Lys
                325                 330                 335

Ala Ala Asp Leu Ser Phe Cys Gln Gln Glu Lys Leu Pro Met Thr Phe
            340                 345                 350

Gln Ser Cys Val Ile Thr Lys Glu Cys Gln Val Ser Glu Trp Ser Glu
            355                 360                 365

Trp Ser Pro Cys Ser Lys Thr Cys His Asp Met Val Ser Pro Ala Gly
370                 375                 380

Thr Arg Val Arg Thr Arg Thr Ile Arg Gln Phe Pro Ile Gly Ser Glu
385                 390                 395                 400

Lys Glu Cys Pro Glu Phe Glu Glu Lys Glu Pro Cys Leu Ser Gln Gly
                405                 410                 415

Asp Gly Val Val Pro Cys Ala Thr Tyr Gly Trp Arg Thr Thr Glu Trp
            420                 425                 430

Thr Glu Cys Arg Val Asp Pro Leu Leu Ser Gln Asp Lys Arg Arg
            435                 440                 445

Gly Asn Gln Thr Ala Leu Cys Gly Gly Ile Gln Thr Arg Glu Val
450                 455                 460

Tyr Cys Val Gln Ala Asn Glu Asn Leu Leu Ser Gln Leu Ser Thr His
465                 470                 475                 480

Lys Asn Lys Glu Ala Ser Lys Pro Met Asp Leu Lys Leu Cys Thr Gly
            485                 490                 495

Pro Ile Pro Asn Thr Thr Gln Leu Cys His Ile Pro Cys Pro Thr Glu
            500                 505                 510

Cys Glu Val Ser Pro Trp Ser Ala Trp Gly Pro Cys Thr Tyr Glu Asn
            515                 520                 525

Cys Asn Asp Gln Gln Gly Lys Lys Gly Phe Lys Leu Arg Lys Arg Arg
530                 535                 540

Ile Thr Asn Glu Pro Thr Gly Gly Ser Gly Val Thr Gly Asn Cys Pro
545                 550                 555                 560
```

-continued

His Leu Leu Glu Ala Ile Pro Cys Glu Glu Pro Ala Cys Tyr Asp Trp
            565                 570                 575

Lys Ala Val Arg Leu Gly Asn Cys Glu Pro Asp Asn Gly Lys Glu Cys
        580                 585                 590

Gly Pro Gly Thr Gln Val Gln Glu Val Val Cys Ile Asn Ser Asp Gly
        595                 600                 605

Glu Glu Val Asp Arg Gln Leu Cys Arg Asp Ala Ile Phe Pro Ile Pro
    610                 615                 620

Val Ala Cys Asp Ala Pro Cys Pro Lys Asp Cys Val Leu Ser Thr Trp
625                 630                 635                 640

Ser Thr Trp Ser Ser Cys Ser His Thr Cys Ser Gly Lys Thr Thr Glu
            645                 650                 655

Gly Lys Gln Ile Arg Ala Arg Ser Ile Leu Ala Tyr Ala Gly Glu Glu
        660                 665                 670

Gly Gly Ile Arg Cys Pro Asn Ser Ser Ala Leu Gln Glu Val Arg Ser
        675                 680                 685

Cys Asn Glu His Pro Cys Thr Val Tyr His Trp Gln Thr Gly Pro Trp
    690                 695                 700

Gly Gln Cys Ile Glu Asp Thr Ser Val Ser Ser Phe Asn Thr Thr Thr
705                 710                 715                 720

Thr Trp Asn Gly Glu Ala Ser Cys Ser Val Gly Met Gln Thr Arg Lys
            725                 730                 735

Val Ile Cys Val Arg Val Asn Val Gly Gln Val Gly Pro Lys Lys Cys
        740                 745                 750

Pro Glu Ser Leu Arg Pro Glu Thr Val Arg Pro Cys Leu Leu Pro Cys
        755                 760                 765

Lys Lys Asp Cys Ile Val Thr Pro Tyr Ser Asp Trp Thr Ser Cys Pro
    770                 775                 780

Ser Ser Cys Lys Glu Gly Asp Ser Ser Ile Arg Lys Gln Ser Arg His
785                 790                 795                 800

Arg Val Ile Ile Gln Leu Pro Ala Asn Gly Gly Arg Asp Cys Thr Asp
            805                 810                 815

Pro Leu Tyr Glu Glu Lys Ala Cys Glu Ala Pro Gln Ala Cys Gln Ser
        820                 825                 830

Tyr Arg Trp Lys Thr His Lys Trp Arg Arg Cys Gln Leu Val Pro Trp
        835                 840                 845

Ser Val Gln Gln Asp Ser Pro Gly Ala Gln Glu Gly Cys Gly Pro Gly
    850                 855                 860

Arg Gln Ala Arg Ala Ile Thr Cys Arg Lys Gln Asp Gly Gly Gln Ala
865                 870                 875                 880

Gly Ile His Glu Cys Leu Gln Tyr Ala Gly Pro Val Pro Ala Leu Thr
            885                 890                 895

Gln Ala Cys Gln Ile Pro Cys Gln Asp Asp Cys Gln Leu Thr Ser Trp
        900                 905                 910

Ser Lys Phe Ser Ser Cys Asn Gly Asp Cys Gly Ala Val Arg Thr Arg
        915                 920                 925

Lys Arg Thr Leu Val Gly Lys Ser Lys Lys Glu Lys Cys Lys Asn
    930                 935                 940

Ser His Leu Tyr Pro Leu Ile Glu Thr Gln Tyr Cys Pro Cys Asp Lys
945                 950                 955                 960

Tyr Asn Ala Gln Pro Val Gly Asn Trp Ser Asp Cys Ile Leu Pro Glu
            965                 970                 975

-continued

```
Gly Lys Val Glu Val Leu Leu Gly Met Lys Val Gln Gly Asp Ile Lys
            980                 985                 990
Glu Cys Gly Gln Gly Tyr Arg Tyr Gln Ala Met Ala Cys Tyr Asp Gln
        995                 1000                1005
Asn Gly Arg Leu Val Glu Thr Ser Arg Cys Asn Ser His Gly Tyr
    1010                1015                1020
Ile Glu Glu Ala Cys Ile Ile Pro Cys Pro Ser Asp Cys Lys Leu
    1025                1030                1035
Ser Glu Trp Ser Asn Trp Ser Arg Cys Ser Lys Ser Cys Gly Ser
    1040                1045                1050
Gly Val Lys Val Arg Ser Lys Trp Leu Arg Glu Lys Pro Tyr Asn
    1055                1060                1065
Gly Gly Arg Pro Cys Pro Lys Leu Asp His Val Asn Gln Ala Gln
    1070                1075                1080
Val Tyr Glu Val Val Pro Cys His Ser Asp Cys Asn Gln Tyr Leu
    1085                1090                1095
Trp Val Thr Glu Pro Trp Ser Ile Cys Lys Val Thr Phe Val Asn
    1100                1105                1110
Met Arg Glu Asn Cys Gly Glu Gly Val Gln Thr Arg Lys Val Arg
    1115                1120                1125
Cys Met Gln Asn Thr Ala Asp Gly Pro Ser Glu His Val Glu Asp
    1130                1135                1140
Tyr Leu Cys Asp Pro Glu Glu Met Pro Leu Gly Ser Arg Val Cys
    1145                1150                1155
Lys Leu Pro Cys Pro Glu Asp Cys Val Ile Ser Glu Trp Gly Pro
    1160                1165                1170
Trp Thr Gln Cys Val Leu Pro Cys Asn Gln Ser Ser Phe Arg Gln
    1175                1180                1185
Arg Ser Ala Asp Pro Ile Arg Gln Pro Ala Asp Glu Gly Arg Ser
    1190                1195                1200
Cys Pro Asn Ala Val Glu Lys Glu Pro Cys Asn Leu Asn Lys Asn
    1205                1210                1215
Cys Tyr His Tyr Asp Tyr Asn Val Thr Asp Trp Ser Thr Cys Gln
    1220                1225                1230
Leu Ser Glu Lys Ala Val Cys Gly Asn Gly Ile Lys Thr Arg Met
    1235                1240                1245
Leu Asp Cys Val Arg Ser Asp Gly Lys Ser Val Asp Leu Lys Tyr
    1250                1255                1260
Cys Glu Ala Leu Gly Leu Glu Lys Asn Trp Gln Met Asn Thr Ser
    1265                1270                1275
Cys Met Val Glu Cys Pro Val Asn Cys Gln Leu Ser Asp Trp Ser
    1280                1285                1290
Pro Trp Ser Glu Cys Ser Gln Thr Cys Gly Leu Thr Gly Lys Met
    1295                1300                1305
Ile Arg Arg Arg Thr Val Thr Gln Pro Phe Gln Gly Asp Gly Arg
    1310                1315                1320
Pro Cys Pro Ser Leu Met Asp Gln Ser Lys Pro Cys Pro Val Lys
    1325                1330                1335
Pro Cys Tyr Arg Trp Gln Tyr Gly Gln Trp Ser Pro Cys Gln Val
    1340                1345                1350
Gln Glu Ala Gln Cys Gly Glu Gly Thr Arg Thr Arg Asn Ile Ser
    1355                1360                1365
```

Cys Val Val Ser Asp Gly Ser Ala Asp Phe Ser Lys Val Val
    1370              1375              1380

Asp Glu Glu Phe Cys Ala Asp Ile Glu Leu Ile Ile Asp Gly Asn
    1385              1390              1395

Lys Asn Met Val Leu Glu Glu Ser Cys Ser Gln Pro Cys Pro Gly
    1400              1405              1410

Asp Cys Tyr Leu Lys Asp Trp Ser Ser Trp Ser Leu Cys Gln Leu
    1415              1420              1425

Thr Cys Val Asn Gly Glu Asp Leu Gly Phe Gly Gly Ile Gln Val
    1430              1435              1440

Arg Ser Arg Pro Val Ile Ile Gln Glu Leu Glu Asn Gln His Leu
    1445              1450              1455

Cys Pro Glu Gln Met Leu Glu Thr Lys Ser Cys Tyr Asp Gly Gln
    1460              1465              1470

Cys Tyr Glu Tyr Lys Trp Met Ala Ser Ala Trp Lys Gly Ser Ser
    1475              1480              1485

Arg Thr Val Trp Cys Gln Arg Ser Asp Gly Ile Asn Val Thr Gly
    1490              1495              1500

Gly Cys Leu Val Met Ser Gln Pro Asp Ala Asp Arg Ser Cys Asn
    1505              1510              1515

Pro Pro Cys Ser Gln Pro His Ser Tyr Cys Ser Glu Thr Lys Thr
    1520              1525              1530

Cys His Cys Glu Glu Gly Tyr Thr Glu Val Met Ser Ser Asn Ser
    1535              1540              1545

Thr Leu Glu Gln Cys Thr Leu Ile Pro Val Val Val Leu Pro Thr
    1550              1555              1560

Met Glu Asp Lys Arg Gly Asp Val Lys Thr Ser Arg Ala Val His
    1565              1570              1575

Pro Thr Gln Pro Ser Ser Asn Pro Ala Gly Arg Gly Arg Thr Trp
    1580              1585              1590

Phe Leu Gln Pro Phe Gly Pro Asp Gly Arg Leu Lys Thr Trp Val
    1595              1600              1605

Tyr Gly Val Ala Ala Gly Ala Phe Val Leu Leu Ile Phe Ile Val
    1610              1615              1620

Ser Met Ile Tyr Leu Ala Cys Lys Lys Pro Lys Lys Pro Gln Arg
    1625              1630              1635

Arg Gln Asn Asn Arg Leu Lys Pro Leu Thr Leu Ala Tyr Asp Gly
    1640              1645              1650

Asp Ala Asp Met
    1655

<210> SEQ ID NO 11
<211> LENGTH: 607
<212> TYPE: PRT
<213> ORGANISM: Artificial Sequence
<220> FEATURE:
<223> OTHER INFORMATION: SEQ ID NO 11 artificial antigen

<400> SEQUENCE: 11

Met Glu Leu Val Arg Arg Leu Met Pro Leu Thr Leu Leu Ile Leu Ser
1               5                   10                  15

Cys Leu Ala Glu Leu Thr Met Ala Glu Ala Glu Gly Asn Ala Ser Cys
                20                  25                  30

Thr Val Ser Leu Gly Gly Ala Asn Met Ala Glu Thr His Lys Ala Met
            35                  40                  45

-continued

```
Ile Leu Gln Leu Asn Pro Ser Glu Asn Cys Thr Trp Thr Ile Glu Arg
 50                  55                  60
Pro Glu Asn Lys Ser Ile Arg Ile Ile Phe Ser Tyr Val Gln Leu Asp
 65                  70                  75                  80
Pro Asp Gly Ser Cys Glu Ser Glu Asn Ile Lys Val Phe Asp Gly Thr
                 85                  90                  95
Ser Ser Asn Gly Pro Leu Leu Gly Gln Val Cys Ser Lys Asn Asp Tyr
                100                 105                 110
Val Pro Val Phe Glu Ser Ser Ser Thr Leu Thr Phe Gln Ile Val
                115                 120                 125
Thr Asp Ser Ala Arg Ile Gln Arg Thr Val Phe Val Phe Tyr Tyr Phe
130                 135                 140
Phe Ser Pro Asn Ile Ser Ile Pro Asn Cys Gly Gly Tyr Leu Asp Thr
145                 150                 155                 160
Leu Glu Gly Ser Phe Thr Ser Pro Asn Tyr Pro Lys Pro His Pro Glu
                165                 170                 175
Leu Ala Tyr Cys Val Trp His Ile Gln Val Glu Lys Asp Tyr Lys Ile
                180                 185                 190
Lys Leu Asn Phe Lys Glu Ile Phe Leu Glu Ile Asp Lys Gln Cys Lys
                195                 200                 205
Phe Asp Phe Leu Ala Ile Tyr Asp Gly Pro Ser Thr Asn Ser Gly Leu
210                 215                 220
Ile Gly Gln Val Cys Gly Arg Val Thr Pro Thr Phe Glu Ser Ser Ser
225                 230                 235                 240
Asn Ser Leu Thr Val Val Leu Ser Thr Asp Tyr Ala Asn Ser Tyr Arg
                245                 250                 255
Gly Phe Ser Ala Ser Tyr Thr Ser Ile Tyr Ala Glu Asn Ile Asn Thr
                260                 265                 270
Thr Ser Leu Thr Cys Ser Ser Asp Arg Met Arg Val Ile Ile Ser Lys
                275                 280                 285
Ser Tyr Leu Glu Ala Phe Asn Ser Asn Gly Asn Asn Leu Gln Leu Lys
290                 295                 300
Asp Pro Thr Cys Arg Pro Lys Leu Ser Asn Val Val Glu Phe Ser Val
305                 310                 315                 320
Pro Leu Asn Gly Cys Gly Thr Ile Arg Lys Val Glu Asp Gln Ser Ile
                325                 330                 335
Thr Tyr Thr Asn Ile Ile Thr Phe Ser Ala Ser Ser Thr Ser Glu Val
                340                 345                 350
Ile Thr Arg Gln Lys Gln Leu Gln Ile Val Lys Cys Glu Met Gly
                355                 360                 365
His Asn Ser Thr Val Glu Ile Ile Tyr Ile Thr Glu Asp Asp Val Ile
370                 375                 380
Gln Ser Gln Asn Ala Leu Gly Lys Tyr Asn Thr Ser Met Ala Leu Phe
385                 390                 395                 400
Glu Ser Asn Ser Phe Glu Lys Thr Ile Leu Glu Ser Pro Tyr Tyr Val
                405                 410                 415
Asp Leu Asn Gln Thr Leu Phe Val Gln Val Ser Leu His Thr Ser Asp
                420                 425                 430
Pro Asn Leu Val Val Phe Leu Asp Thr Cys Arg Ala Ser Pro Thr Ser
                435                 440                 445
Asp Phe Ala Ser Pro Thr Tyr Asp Leu Ile Lys Ser Gly Cys Ser Arg
450                 455                 460
```

```
Asp Glu Thr Cys Lys Val Tyr Pro Leu Phe His Tyr Gly Arg Phe
465                 470                 475                 480

Gln Phe Asn Ala Phe Lys Phe Leu Arg Ser Met Ser Ser Val Tyr Leu
                485                 490                 495

Gln Cys Lys Val Leu Ile Cys Asp Ser Ser Asp His Gln Ser Arg Cys
            500                 505                 510

Asn Gln Gly Cys Val Ser Arg Ser Lys Arg Asp Ile Ser Ser Tyr Lys
            515                 520                 525

Trp Lys Thr Asp Ser Ile Ile Gly Pro Ile Arg Leu Lys Arg Asp Arg
530                 535                 540

Ser Ala Ser Gly Asn Ser Gly Phe Gln His Glu Thr His Ala Glu Glu
545                 550                 555                 560

Thr Pro Asn Gln Pro Phe Asn Ser Val His Leu Phe Ser Phe Met Val
                565                 570                 575

Leu Ala Leu Asn Val Val Thr Val Ala Thr Ile Thr Val Arg His Phe
            580                 585                 590

Val Asn Gln Arg Ala Asp Tyr Lys Tyr Gln Lys Leu Gly Asn Tyr
            595                 600                 605

<210> SEQ ID NO 12
<211> LENGTH: 530
<212> TYPE: PRT
<213> ORGANISM: Artificial Sequence
<220> FEATURE:
<223> OTHER INFORMATION: SEQ ID NO 12 artificial antigen

<400> SEQUENCE: 12

Met Glu Arg Met Val Gly Ser Gly Leu Leu Trp Leu Ala Leu Val Ser
1               5                   10                  15

Cys Ile Leu Thr Gln Ala Ser Ala Val Gln Arg Gly Tyr Gly Asn Pro
                20                  25                  30

Ile Glu Ala Ser Ser Tyr Gly Leu Asp Leu Asp Cys Gly Ala Pro Gly
            35                  40                  45

Thr Pro Glu Ala His Val Cys Phe Asp Pro Cys Gln Asn Tyr Thr Leu
50                  55                  60

Leu Asp Glu Pro Phe Arg Ser Thr Glu Asn Ser Ala Gly Ser Gln Gly
65                  70                  75                  80

Cys Asp Lys Asn Met Ser Gly Trp Tyr Arg Phe Val Gly Glu Gly Gly
                85                  90                  95

Val Arg Met Ser Glu Thr Cys Val Gln Val His Arg Cys Gln Thr Asp
                100                 105                 110

Ala Pro Met Trp Leu Asn Gly Thr His Pro Ala Leu Gly Asp Gly Ile
            115                 120                 125

Thr Asn His Thr Ala Cys Ala His Trp Ser Gly Asn Cys Cys Phe Trp
130                 135                 140

Lys Thr Glu Val Leu Val Lys Ala Cys Pro Gly Gly Tyr His Val Tyr
145                 150                 155                 160

Arg Leu Glu Gly Thr Pro Trp Cys Asn Leu Arg Tyr Cys Thr Asp Pro
                165                 170                 175

Ser Thr Val Glu Asp Lys Cys Glu Lys Ala Cys Arg Pro Glu Glu Glu
            180                 185                 190

Cys Leu Ala Leu Asn Ser Thr Trp Gly Cys Phe Cys Arg Gln Asp Leu
            195                 200                 205

Asn Ser Ser Asp Val His Ser Leu Gln Pro Gln Leu Asp Cys Gly Pro
210                 215                 220
```

-continued

```
Arg Glu Ile Lys Val Lys Val Asp Lys Cys Leu Leu Gly Gly Leu Gly
225                 230                 235                 240

Leu Gly Glu Glu Val Ile Ala Tyr Leu Arg Asp Pro Asn Cys Ser Ser
            245                 250                 255

Ile Leu Gln Thr Glu Glu Arg Asn Trp Val Ser Val Thr Ser Pro Val
        260                 265                 270

Gln Ala Ser Ala Cys Arg Asn Ile Leu Glu Arg Asn Gln Thr His Ala
275                 280                 285

Ile Tyr Lys Asn Thr Leu Ser Leu Val Asn Asp Phe Ile Ile Arg Asp
    290                 295                 300

Thr Ile Leu Asn Ile Asn Phe Gln Cys Ala Tyr Pro Leu Asp Met Lys
305                 310                 315                 320

Val Ser Leu Gln Ala Ala Leu Gln Pro Ile Val Ser Ser Leu Asn Val
                325                 330                 335

Ser Val Asp Gly Asn Gly Glu Phe Ile Val Arg Met Ala Leu Phe Gln
            340                 345                 350

Asp Gln Asn Tyr Thr Asn Pro Tyr Glu Gly Asp Ala Val Glu Leu Ser
        355                 360                 365

Val Glu Ser Val Leu Tyr Val Gly Ala Ile Leu Glu Gln Gly Asp Thr
370                 375                 380

Ser Arg Phe Asn Leu Val Leu Arg Asn Cys Tyr Ala Thr Pro Thr Glu
385                 390                 395                 400

Asp Lys Ala Asp Leu Val Lys Tyr Phe Ile Ile Arg Asn Ser Cys Ser
                405                 410                 415

Asn Gln Arg Asp Ser Thr Ile His Val Glu Glu Asn Gly Gln Ser Ser
            420                 425                 430

Glu Ser Arg Phe Ser Val Gln Met Phe Met Phe Ala Gly His Tyr Asp
        435                 440                 445

Leu Val Phe Leu His Cys Glu Ile His Leu Cys Asp Ser Leu Asn Glu
    450                 455                 460

Gln Cys Gln Pro Ser Cys Ser Arg Ser Gln Val Arg Ser Glu Val Pro
465                 470                 475                 480

Ala Ile Asp Leu Ala Arg Val Leu Asp Leu Gly Pro Ile Thr Arg Arg
                485                 490                 495

Gly Ala Gln Ser Pro Gly Val Met Asn Gly Thr Pro Ser Thr Ala Gly
            500                 505                 510

Phe Leu Val Ala Trp Pro Met Val Leu Leu Thr Val Leu Leu Ala Trp
        515                 520                 525

Leu Phe
530
```

<210> SEQ ID NO 13
<211> LENGTH: 368
<212> TYPE: PRT
<213> ORGANISM: Artificial Sequence
<220> FEATURE:
<223> OTHER INFORMATION: SEQ ID NO 13 artificial antigen

<400> SEQUENCE: 13

```
Met Glu Pro Gly Gln Pro Arg Glu Pro Gln Glu Pro Arg Glu Pro Gly
1               5                   10                  15

Pro Gly Ala Glu Thr Ala Ala Ala Pro Val Trp Glu Glu Ala Lys Ile
            20                  25                  30

Phe Tyr Asp Asn Leu Ala Pro Lys Lys Pro Lys Ser Pro Lys Pro
        35                  40                  45
```

```
Gln Asn Ala Val Thr Ile Ala Val Ser Ser Arg Ala Leu Phe Arg Met
     50                  55                  60

Asp Glu Gln Gln Ile Tyr Thr Glu Gln Gly Val Glu Glu Tyr Val
 65                  70                  75                  80

Arg Tyr Gln Leu Glu His Glu Asn Glu Pro Phe Ser Pro Gly Pro Ala
                 85                  90                  95

Phe Pro Phe Val Lys Ala Leu Glu Ala Val Asn Arg Arg Leu Arg Glu
                100                 105                 110

Leu Tyr Pro Asp Ser Glu Asp Val Phe Asp Ile Val Leu Met Thr Asn
                115                 120                 125

Asn His Ala Gln Val Gly Val Arg Leu Ile Asn Ser Ile Asn His Tyr
    130                 135                 140

Asp Leu Phe Ile Glu Arg Phe Cys Met Thr Gly Gly Asn Ser Pro Ile
145                 150                 155                 160

Cys Tyr Leu Lys Ala Tyr His Thr Asn Leu Tyr Leu Ser Ala Asp Ala
                165                 170                 175

Glu Lys Val Arg Glu Ala Ile Asp Glu Gly Ile Ala Ala Ala Thr Ile
                180                 185                 190

Phe Ser Pro Ser Arg Asp Val Val Ser Gln Ser Gln Leu Arg Val
                195                 200                 205

Ala Phe Asp Gly Asp Ala Val Leu Phe Ser Asp Glu Ser Glu Arg Ile
    210                 215                 220

Val Lys Ala His Gly Leu Asp Arg Phe Phe Glu His Glu Lys Ala His
225                 230                 235                 240

Glu Asn Lys Pro Leu Ala Gln Gly Pro Leu Lys Gly Phe Leu Glu Ala
                245                 250                 255

Leu Gly Arg Leu Gln Lys Lys Phe Tyr Ser Lys Gly Leu Arg Leu Glu
                260                 265                 270

Cys Pro Ile Arg Thr Tyr Leu Val Thr Ala Arg Ser Ala Ala Ser Ser
                275                 280                 285

Gly Ala Arg Ala Leu Lys Thr Leu Arg Ser Trp Gly Leu Glu Thr Asp
    290                 295                 300

Glu Ala Leu Phe Leu Ala Gly Ala Pro Lys Gly Pro Leu Leu Glu Lys
305                 310                 315                 320

Ile Arg Pro His Ile Phe Phe Asp Asp Gln Met Phe His Val Ala Gly
                325                 330                 335

Ala Gln Glu Met Gly Thr Val Ala Ala His Val Pro Tyr Gly Val Ala
                340                 345                 350

Gln Thr Pro Arg Arg Thr Ala Pro Ala Lys Gln Ala Pro Ser Ala Gln
                355                 360                 365
```

<210> SEQ ID NO 14
<211> LENGTH: 1724
<212> TYPE: PRT
<213> ORGANISM: Artificial Sequence
<220> FEATURE:
<223> OTHER INFORMATION: SEQ ID NO 14 LAMA3

<400> SEQUENCE: 14

```
Met Pro Pro Ala Val Arg Arg Ser Ala Cys Ser Met Gly Trp Leu Trp
 1               5                  10                  15

Ile Phe Gly Ala Ala Leu Gly Gln Cys Leu Gly Tyr Ser Ser Gln Gln
                20                  25                  30

Gln Arg Val Pro Phe Leu Gln Pro Pro Gly Gln Ser Gln Leu Gln Ala
                35                  40                  45
```

```
Ser Tyr Val Glu Phe Arg Pro Ser Gln Gly Cys Ser Pro Gly Tyr Tyr
 50                  55                  60

Arg Asp His Lys Gly Leu Tyr Thr Gly Arg Cys Val Pro Cys Asn Cys
 65                  70                  75                  80

Asn Gly His Ser Asn Gln Cys Gln Asp Gly Ser Gly Ile Cys Val Asn
                 85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
            115                 120                 125

His Thr Asn Ser Phe Ala Thr Gly Cys Val Val Asn Gly Gly Asp Val
130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
            195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
                260                 265                 270

Ser Asn His Gly Ser Lys Ile Glu Gly Leu Glu Arg Glu Leu Thr Asp
            275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
                325                 330                 335

Ile Leu Leu Lys Gln Ile Ser Gly Thr Asp Gly Glu Gly Asn Asn Val
                340                 345                 350

Pro Ser Gly Asp Phe Ser Arg Glu Trp Ala Glu Ala Gln Arg Met Met
            355                 360                 365

Arg Glu Leu Arg Asn Arg Asn Phe Gly Lys His Leu Arg Glu Ala Glu
    370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
                405                 410                 415

Asp Ser Leu Asn Glu Tyr Glu Ala Lys Leu Ser Asp Leu Arg Ala Arg
            420                 425                 430

Leu Gln Glu Ala Ala Gln Ala Lys Gln Ala Asn Gly Leu Asn Gln
    435                 440                 445

Glu Asn Glu Arg Ala Leu Gly Ala Ile Gln Arg Gln Val Lys Glu Ile
450                 455                 460
```

-continued

```
Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
            485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
            515                 520                 525

Leu Val Glu Glu Ala Glu Lys His Ala Arg Ser Leu Gln Glu Leu Ala
            530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
                565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
            610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
                645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
                675                 680                 685

Ile Thr Asp Glu Val Leu Asp Gly Leu Asn Pro Ile Gln Thr Asp Val
            690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
                725                 730                 735

Leu Pro Asp Leu Trp Arg Lys Ile Glu Ser Ile Asn Gln Gln Leu Leu
            740                 745                 750

Pro Leu Gly Asn Ile Ser Asp Asn Met Asp Arg Ile Arg Glu Leu Ile
            755                 760                 765

Gln Gln Ala Arg Asp Ala Ala Ser Lys Val Ala Val Pro Met Arg Phe
770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
                805                 810                 815

Arg Glu Asn Gly Gly Thr Glu Asn Met Phe Val Met Tyr Leu Gly Asn
            820                 825                 830

Lys Asp Ala Ser Arg Asp Tyr Ile Gly Met Ala Val Val Asp Gly Gln
            835                 840                 845

Leu Thr Cys Val Tyr Asn Leu Gly Asp Arg Glu Ala Glu Leu Gln Val
            850                 855                 860

Asp Gln Ile Leu Thr Lys Ser Glu Thr Lys Glu Ala Val Met Asp Arg
865                 870                 875                 880
```

```
Val Lys Phe Gln Arg Ile Tyr Gln Phe Ala Arg Leu Asn Tyr Thr Lys
            885                 890                 895

Gly Ala Thr Ser Ser Lys Pro Glu Thr Pro Gly Val Tyr Asp Met Asp
            900                 905                 910

Gly Arg Asn Ser Asn Thr Leu Leu Asn Leu Asp Pro Glu Asn Val Val
            915                 920                 925

Phe Tyr Val Gly Gly Tyr Pro Pro Asp Phe Lys Leu Pro Ser Arg Leu
            930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
            965                 970                 975

Thr Glu Val Glu Pro Cys Arg Arg Arg Lys Glu Glu Ser Asp Lys Asn
            980                 985                 990

Tyr Phe Glu Gly Thr Gly Tyr Ala Arg Val Pro Thr Gln Pro His Ala
            995                 1000                1005

Pro Ile Pro Thr Phe Gly Gln Thr Ile Gln Thr Thr Val Asp Arg
            1010                1015                1020

Gly Leu Leu Phe Phe Ala Glu Asn Gly Asp Arg Phe Ile Ser Leu
            1025                1030                1035

Asn Ile Glu Asp Gly Lys Leu Met Val Arg Tyr Lys Leu Asn Ser
            1040                1045                1050

Glu Leu Pro Lys Glu Arg Gly Val Gly Asp Ala Ile Asn Asn Gly
            1055                1060                1065

Arg Asp His Ser Ile Gln Ile Lys Ile Gly Lys Leu Gln Lys Arg
            1070                1075                1080

Met Trp Ile Asn Val Asp Val Gln Asn Thr Ile Ile Asp Gly Glu
            1085                1090                1095

Val Phe Asp Phe Ser Thr Tyr Tyr Leu Gly Gly Ile Pro Ile Ala
            1100                1105                1110

Ile Arg Glu Arg Phe Asn Ile Ser Thr Pro Ala Phe Arg Gly Cys
            1115                1120                1125

Met Lys Asn Leu Lys Lys Thr Ser Gly Val Val Arg Leu Asn Asp
            1130                1135                1140

Thr Val Gly Val Thr Lys Lys Cys Ser Glu Asp Trp Lys Leu Val
            1145                1150                1155

Arg Ser Ala Ser Phe Ser Arg Gly Gly Gln Leu Ser Phe Thr Asp
            1160                1165                1170

Leu Gly Leu Pro Pro Thr Asp His Leu Gln Ala Ser Phe Gly Phe
            1175                1180                1185

Gln Thr Phe Gln Pro Ser Gly Ile Leu Leu Asp His Gln Thr Trp
            1190                1195                1200

Thr Arg Asn Leu Gln Val Thr Leu Glu Asp Gly Tyr Ile Glu Leu
            1205                1210                1215

Ser Thr Ser Asp Ser Gly Ser Pro Ile Phe Lys Ser Pro Gln Thr
            1220                1225                1230

Tyr Met Asp Gly Leu Leu His Tyr Val Ser Val Ile Ser Asp Asn
            1235                1240                1245

Ser Gly Leu Arg Leu Leu Ile Asp Asp Gln Leu Leu Arg Asn Ser
            1250                1255                1260

Lys Arg Leu Lys His Ile Ser Ser Ser Arg Gln Ser Leu Arg Leu
            1265                1270                1275
```

```
Gly Gly Ser Asn Phe Glu Gly Cys Ile Ser Asn Val Phe Val Gln
    1280                1285                1290

Arg Leu Ser Leu Ser Pro Glu Val Leu Asp Leu Thr Ser Asn Ser
    1295                1300                1305

Leu Lys Arg Asp Val Ser Leu Gly Gly Cys Ser Leu Asn Lys Pro
    1310                1315                1320

Pro Phe Leu Met Leu Leu Lys Gly Ser Thr Arg Phe Asn Lys Thr
    1325                1330                1335

Lys Thr Phe Arg Ile Asn Gln Leu Leu Gln Asp Thr Pro Val Ala
    1340                1345                1350

Ser Pro Arg Ser Val Lys Val Trp Gln Asp Ala Cys Ser Pro Leu
    1355                1360                1365

Pro Lys Thr Gln Ala Asn His Gly Ala Leu Gln Phe Gly Asp Ile
    1370                1375                1380

Pro Thr Ser His Leu Leu Phe Lys Leu Pro Gln Glu Leu Leu Lys
    1385                1390                1395

Pro Arg Ser Gln Phe Ala Val Asp Met Gln Thr Thr Ser Ser Arg
    1400                1405                1410

Gly Leu Val Phe His Thr Gly Thr Lys Asn Ser Phe Met Ala Leu
    1415                1420                1425

Tyr Leu Ser Lys Gly Arg Leu Val Phe Ala Leu Gly Thr Asp Gly
    1430                1435                1440

Lys Lys Leu Arg Ile Lys Ser Lys Glu Lys Cys Asn Asp Gly Lys
    1445                1450                1455

Trp His Thr Val Val Phe Gly His Asp Gly Glu Lys Gly Arg Leu
    1460                1465                1470

Val Val Asp Gly Leu Arg Ala Arg Glu Gly Ser Leu Pro Gly Asn
    1475                1480                1485

Ser Thr Ile Ser Ile Arg Ala Pro Val Tyr Leu Gly Ser Pro Pro
    1490                1495                1500

Ser Gly Lys Pro Lys Ser Leu Pro Thr Asn Ser Phe Val Gly Cys
    1505                1510                1515

Leu Lys Asn Phe Gln Leu Asp Ser Lys Pro Leu Tyr Thr Pro Ser
    1520                1525                1530

Ser Ser Phe Gly Val Ser Ser Cys Leu Gly Gly Pro Leu Glu Lys
    1535                1540                1545

Gly Ile Tyr Phe Ser Glu Glu Gly Gly His Val Val Leu Ala His
    1550                1555                1560

Ser Val Leu Leu Gly Pro Glu Phe Lys Leu Val Phe Ser Ile Arg
    1565                1570                1575

Pro Arg Ser Leu Thr Gly Ile Leu Ile His Ile Gly Ser Gln Pro
    1580                1585                1590

Gly Lys His Leu Cys Val Tyr Leu Glu Ala Gly Lys Val Thr Ala
    1595                1600                1605

Ser Met Asp Ser Gly Ala Gly Gly Thr Ser Thr Ser Val Thr Pro
    1610                1615                1620

Lys Gln Ser Leu Cys Asp Gly Gln Trp His Ser Val Ala Val Thr
    1625                1630                1635

Ile Lys Gln His Ile Leu His Leu Glu Leu Asp Thr Asp Ser Ser
    1640                1645                1650

Tyr Thr Ala Gly Gln Ile Pro Phe Pro Pro Ala Ser Thr Gln Glu
    1655                1660                1665
```

-continued

Pro Leu His Leu Gly Gly Ala Pro Ala Asn Leu Thr Thr Leu Arg
    1670              1675                1680

Ile Pro Val Trp Lys Ser Phe Phe Gly Cys Leu Arg Asn Ile His
    1685              1690                1695

Val Asn His Ile Pro Val Pro Val Thr Glu Ala Leu Glu Val Gln
    1700              1705                1710

Gly Pro Val Ser Leu Asn Gly Cys Pro Asp Gln
    1715              1720

<210> SEQ ID NO 15
<211> LENGTH: 1172
<212> TYPE: PRT
<213> ORGANISM: Artificial Sequence
<220> FEATURE:
<223> OTHER INFORMATION: SEQ ID NO 15 LAMB3

<400> SEQUENCE: 15

Met Arg Pro Phe Phe Leu Leu Cys Phe Ala Leu Pro Gly Leu Leu His
1               5                   10                  15

Ala Gln Gln Ala Cys Ser Arg Gly Ala Cys Tyr Pro Pro Val Gly Asp
            20                  25                  30

Leu Leu Val Gly Arg Thr Arg Phe Leu Arg Ala Ser Ser Thr Cys Gly
        35                  40                  45

Leu Thr Lys Pro Glu Thr Tyr Cys Thr Gln Tyr Gly Glu Trp Gln Met
    50                  55                  60

Lys Cys Cys Lys Cys Asp Ser Arg Gln Pro His Asn Tyr Tyr Ser His
65                  70                  75                  80

Arg Val Glu Asn Val Ala Ser Ser Gly Pro Met Arg Trp Trp Gln
                85                  90                  95

Ser Gln Asn Asp Val Asn Pro Val Ser Leu Gln Leu Asp Leu Asp Arg
            100                 105                 110

Arg Phe Gln Leu Gln Glu Val Met Met Glu Phe Gln Gly Pro Met Pro
        115                 120                 125

Ala Gly Met Leu Ile Glu Arg Ser Ser Asp Phe Gly Lys Thr Trp Arg
    130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
        195                 200                 205

Gln Glu Val Gly Glu Ile Thr Asn Leu Arg Val Asn Phe Thr Arg Leu
    210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Pro Ser Thr Ala
            260                 265                 270

Val Gln Val His Asp Val Cys Val Cys Gln His Asn Thr Ala Gly Pro
        275                 280                 285

Asn Cys Glu Arg Cys Ala Pro Phe Tyr Asn Asn Arg Pro Trp Arg Pro
    290                 295                 300

```
Ala Glu Gly Gln Asp Ala His Glu Cys Gln Arg Cys Asp Cys Asn Gly
305                 310                 315                 320

His Ser Glu Thr Cys His Phe Asp Pro Ala Val Phe Ala Ala Ser Gln
            325                 330                 335

Gly Ala Tyr Gly Gly Val Cys Asp Asn Cys Arg Asp His Thr Glu Gly
            340                 345                 350

Lys Asn Cys Glu Arg Cys Gln Leu His Tyr Phe Arg Asn Arg Arg Pro
            355                 360                 365

Gly Ala Ser Ile Gln Glu Thr Cys Ile Ser Cys Glu Cys Asp Pro Asp
            370                 375                 380

Gly Ala Val Pro Gly Ala Pro Cys Asp Pro Val Thr Gly Gln Cys Val
385                 390                 395                 400

Cys Lys Glu His Val Gln Gly Glu Arg Cys Asp Leu Cys Lys Pro Gly
                405                 410                 415

Phe Thr Gly Leu Thr Tyr Ala Asn Pro Gln Gly Cys His Arg Cys Asp
                420                 425                 430

Cys Asn Ile Leu Gly Ser Arg Arg Asp Met Pro Cys Asp Glu Glu Ser
            435                 440                 445

Gly Arg Cys Leu Cys Leu Pro Asn Val Val Gly Pro Lys Cys Asp Gln
450                 455                 460

Cys Ala Pro Tyr His Trp Lys Leu Ala Ser Gly Gln Gly Cys Glu Pro
465                 470                 475                 480

Cys Ala Cys Asp Pro His Asn Ser Leu Ser Pro Gln Cys Asn Gln Phe
                485                 490                 495

Thr Gly Gln Cys Pro Cys Arg Glu Gly Phe Gly Gly Leu Met Cys Ser
            500                 505                 510

Ala Ala Ala Ile Arg Gln Cys Pro Asp Arg Thr Tyr Gly Asp Val Ala
            515                 520                 525

Thr Gly Cys Arg Ala Cys Asp Cys Asp Phe Arg Gly Thr Glu Gly Pro
            530                 535                 540

Gly Cys Asp Lys Ala Ser Gly Arg Cys Leu Cys Arg Pro Gly Leu Thr
545                 550                 555                 560

Gly Pro Arg Cys Asp Gln Cys Gln Arg Gly Tyr Cys Asn Arg Tyr Pro
            565                 570                 575

Val Cys Val Ala Cys His Pro Cys Phe Gln Thr Tyr Asp Ala Asp Leu
            580                 585                 590

Arg Glu Gln Ala Leu Arg Phe Gly Arg Leu Arg Asn Ala Thr Ala Ser
            595                 600                 605

Leu Trp Ser Gly Pro Gly Leu Glu Asp Arg Gly Leu Ala Ser Arg Ile
            610                 615                 620

Leu Asp Ala Lys Ser Lys Ile Glu Gln Ile Arg Ala Val Leu Ser Ser
625                 630                 635                 640

Pro Ala Val Thr Glu Gln Glu Val Ala Gln Val Ala Ser Ala Ile Leu
                645                 650                 655

Ser Leu Arg Arg Thr Leu Gln Gly Leu Gln Leu Asp Leu Pro Leu Glu
                660                 665                 670

Glu Glu Thr Leu Ser Leu Pro Arg Asp Leu Glu Ser Leu Asp Arg Ser
            675                 680                 685

Phe Asn Gly Leu Leu Thr Met Tyr Gln Arg Lys Arg Glu Gln Phe Glu
            690                 695                 700

Lys Ile Ser Ser Ala Asp Pro Ser Gly Ala Phe Arg Met Leu Ser Thr
705                 710                 715                 720
```

-continued

Ala Tyr Glu Gln Ser Ala Gln Ala Ala Gln Gln Val Ser Asp Ser Ser
                725                 730                 735

Arg Leu Leu Asp Gln Leu Arg Asp Ser Arg Arg Glu Ala Glu Arg Leu
            740                 745                 750

Val Arg Gln Ala Gly Gly Gly Gly Thr Gly Ser Pro Lys Leu Val
        755                 760                 765

Ala Leu Arg Leu Glu Met Ser Ser Leu Pro Asp Leu Thr Pro Thr Phe
        770                 775                 780

Asn Lys Leu Cys Gly Asn Ser Arg Gln Met Ala Cys Thr Pro Ile Ser
785                 790                 795                 800

Cys Pro Gly Glu Leu Cys Pro Gln Asp Asn Gly Thr Ala Cys Gly Ser
                805                 810                 815

Arg Cys Arg Gly Val Leu Pro Arg Ala Gly Gly Ala Phe Leu Met Ala
            820                 825                 830

Gly Gln Val Ala Glu Gln Leu Arg Gly Phe Asn Ala Gln Leu Gln Arg
        835                 840                 845

Thr Arg Gln Met Ile Arg Ala Ala Glu Ser Ala Ser Gln Ile Gln
        850                 855                 860

Ser Ser Ala Gln Arg Leu Glu Thr Gln Val Ser Ala Ser Arg Ser Gln
865                 870                 875                 880

Met Glu Glu Asp Val Arg Arg Thr Arg Leu Leu Ile Gln Val Arg
                885                 890                 895

Asp Phe Leu Thr Asp Pro Asp Thr Asp Ala Ala Thr Ile Gln Glu Val
            900                 905                 910

Ser Glu Ala Val Leu Ala Leu Trp Leu Pro Thr Asp Ser Ala Thr Val
        915                 920                 925

Leu Gln Lys Met Asn Glu Ile Gln Ala Ile Ala Ala Arg Leu Pro Asn
        930                 935                 940

Val Asp Leu Val Leu Ser Gln Thr Lys Gln Asp Ile Ala Arg Ala Arg
945                 950                 955                 960

Arg Leu Gln Ala Glu Ala Glu Ala Arg Ser Arg Ala His Ala Val
                965                 970                 975

Glu Gly Gln Val Glu Asp Val Val Gly Asn Leu Arg Gln Gly Thr Val
            980                 985                 990

Ala Leu Gln Glu Ala Gln Asp Thr Met Gln Gly Thr Ser Arg Ser Leu
        995                 1000                1005

Arg Leu Ile Gln Asp Arg Val Ala Glu Val Gln Gln Val Leu Arg
        1010                1015                1020

Pro Ala Glu Lys Leu Val Thr Ser Met Thr Lys Gln Leu Gly Asp
        1025                1030                1035

Phe Trp Thr Arg Met Glu Glu Leu Arg His Gln Ala Arg Gln Gln
        1040                1045                1050

Gly Ala Glu Ala Val Gln Ala Gln Gln Leu Ala Glu Gly Ala Ser
        1055                1060                1065

Glu Gln Ala Leu Ser Ala Gln Glu Gly Phe Glu Arg Ile Lys Gln
        1070                1075                1080

Lys Tyr Ala Glu Leu Lys Asp Arg Leu Gly Gln Ser Ser Met Leu
        1085                1090                1095

Gly Glu Gln Gly Ala Arg Ile Gln Ser Val Lys Thr Glu Ala Glu
        1100                1105                1110

Glu Leu Phe Gly Glu Thr Met Glu Met Met Asp Arg Met Lys Asp
        1115                1120                1125

```
Met Glu Leu Glu Leu Leu Arg Gly Ser Gln Ala Ile Met Leu Arg
    1130                1135                1140

Ser Ala Asp Leu Thr Gly Leu Glu Lys Arg Val Glu Gln Ile Arg
    1145                1150                1155

Asp His Ile Asn Gly Arg Val Leu Tyr Tyr Ala Thr Cys Lys
    1160                1165                1170

<210> SEQ ID NO 16
<211> LENGTH: 1111
<212> TYPE: PRT
<213> ORGANISM: Artificial Sequence
<220> FEATURE:
<223> OTHER INFORMATION: SEQ ID NO 16 LAMC2-short

<400> SEQUENCE: 16

Met Pro Ala Leu Trp Leu Gly Cys Cys Leu Cys Phe Ser Leu Leu
1               5                   10                  15

Pro Ala Ala Arg Ala Thr Ser Arg Arg Glu Val Cys Asp Cys Asn
                20                  25                  30

Gly Lys Ser Arg Gln Cys Ile Phe Asp Arg Glu Leu His Arg Gln
                35                  40                  45

Thr Gly Asn Gly Phe Arg Cys Leu Asn Cys Asn Asp Asn Thr Asp
    50                  55                      60

Gly Ile His Cys Glu Lys Cys Lys Asn Gly Phe Tyr Arg His Arg
65                  70                      75              80

Glu Arg Asp Arg Cys Leu Pro Cys Asn Cys Asn Ser Lys Gly Ser
                                85                      90

Leu Ser Ala Arg Cys Asp Asn Ser Gly Arg Cys Ser Cys Lys Pro
            95                      100                 105

Gly Val Thr Gly Ala Arg Cys Asp Arg Cys Leu Pro Gly Phe His
                    110                     115                 120

Met Leu Thr Asp Ala Gly Cys Thr Gln Asp Gln Arg Leu Leu Asp
                125                     130                     135

Ser Lys Cys Asp Cys Asp Pro Ala Gly Ile Ala Gly Pro Cys Asp
            140                     145                     150

Ala Gly Arg Cys Val Cys Lys Pro Ala Val Thr Gly Glu Arg Cys
                    155                     160                     165

Asp Arg Cys Arg Ser Gly Tyr Tyr Asn Leu Asp Gly Gly Asn Pro
                        170                     175                 180

Glu Gly Cys Thr Gln Cys Phe Cys Tyr Gly His Ser Ala Ser Cys
                    185                 190                     195

Arg Ser Ser Ala Glu Tyr Ser Val His Lys Ile Thr Ser Thr Phe
                200                     205                 210

His Gln Asp Val Asp Gly Trp Lys Ala Val Gln Arg Asn Gly Ser
                215                     220                     225

Pro Ala Lys Leu Gln Trp Ser Gln Arg His Gln Asp Val Phe Ser
            230                     235                     240

Ser Ala Gln Arg Leu Asp Pro Val Tyr Phe Val Ala Pro Ala Lys
                245                     250                     255

Phe Leu Gly Asn Gln Gln Val Ser Tyr Gly Gln Ser Leu Ser Phe
                260                     265                     270

Asp Tyr Arg Val Asp Arg Gly Gly Arg His Pro Ser Ala His Asp
                    275                     280                     285

Val Ile Leu Glu Gly Ala Gly Leu Arg Ile Thr Ala Pro Leu Met
                            290                     295                 300

Pro Leu Gly Lys Thr Leu Pro Cys Gly Leu Thr Lys Thr Tyr Thr
                305                     310                     315

Phe Arg Leu Asn
                    320
```

-continued

```
Glu His Pro Ser Asn Asn Trp Ser Pro Gln Leu Ser Tyr Phe Glu Tyr
            325                 330                 335
Arg Arg Leu Leu Arg Asn Leu Thr Ala Leu Arg Ile Arg Ala Thr Tyr
        340                 345                 350
Gly Glu Tyr Ser Thr Gly Tyr Ile Asp Asn Val Thr Leu Ile Ser Ala
            355                 360                 365
Arg Pro Val Ser Gly Ala Pro Ala Pro Trp Val Glu Gln Cys Ile Cys
370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                405                 410                 415
Asn Cys Gln Gly Gly Ala Cys Asp Pro Asp Thr Gly Asp Cys Tyr
            420                 425                 430
Ser Gly Asp Glu Asn Pro Asp Ile Glu Cys Ala Asp Cys Pro Ile Gly
            435                 440                 445
Phe Tyr Asn Asp Pro His Asp Pro Arg Ser Cys Lys Pro Cys Pro Cys
        450                 455                 460
His Asn Gly Phe Ser Cys Ser Val Met Pro Glu Thr Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly His Gly Pro Val Arg
            500                 505                 510
Pro Cys Gln Pro Cys Gln Cys Asn Asn Asn Val Asp Pro Ser Ala Ser
        515                 520                 525
Gly Asn Cys Asp Arg Leu Thr Gly Arg Cys Leu Lys Cys Ile His Asn
    530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                565                 570                 575
Pro Met Gly Ser Glu Pro Val Gly Cys Arg Ser Asp Gly Thr Cys Val
            580                 585                 590
Cys Lys Pro Gly Phe Gly Gly Pro Asn Cys Glu His Gly Ala Phe Ser
        595                 600                 605
Cys Pro Ala Cys Tyr Asn Gln Val Lys Ile Gln Met Asp Gln Phe Met
        610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
                645                 650                 655
Glu Gln Ala Leu Gln Asp Ile Leu Arg Asp Ala Gln Ile Ser Glu Gly
            660                 665                 670
Ala Ser Arg Ser Leu Gly Leu Gln Leu Ala Lys Val Arg Ser Gln Glu
        675                 680                 685
Asn Ser Tyr Gln Ser Arg Leu Asp Asp Leu Lys Met Thr Val Glu Arg
    690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
```

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
        770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
        835                 840                 845

Leu Arg Leu Leu Asp Ser Val Ser Arg Leu Gln Gly Val Ser Asp Gln
        850                 855                 860

Ser Phe Gln Val Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Ala Gln Gln Leu Leu Gln Asn
            900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
        930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
        995                 1000                1005

Asn Gly Ala Gly Glu Ala Leu Glu Ile Ser Ser Glu Ile Glu Gln
    1010                1015                1020

Glu Ile Gly Ser Leu Asn Leu Glu Ala Asn Val Thr Ala Asp Gly
    1025                1030                1035

Ala Leu Ala Met Glu Lys Gly Leu Ala Ser Leu Lys Ser Glu Met
    1040                1045                1050

Arg Glu Val Glu Gly Glu Leu Glu Arg Lys Glu Leu Glu Phe Asp
    1055                1060                1065

Thr Asn Met Asp Ala Val Gln Met Val Ile Thr Glu Ala Gln Lys
    1070                1075                1080

Val Asp Thr Arg Ala Lys Asn Ala Gly Val Thr Ile Gln Asp Thr
    1085                1090                1095

Leu Asn Thr Leu Asp Gly Leu Leu His Leu Met Gly Met
    1100                1105                1110

<210> SEQ ID NO 17
<211> LENGTH: 1800
<212> TYPE: PRT
<213> ORGANISM: Artificial Sequence
<220> FEATURE:
<223> OTHER INFORMATION: SEQ ID NO 17 b4-Integrin-His

```
<400> SEQUENCE: 17

Met Ala Gly Pro Arg Pro Ser Pro Trp Ala Arg Leu Leu Leu Ala Ala
1               5                   10                  15

Leu Ile Ser Val Ser Leu Ser Gly Thr Leu Ala Asn Arg Cys Lys Lys
            20                  25                  30

Ala Pro Val Lys Ser Cys Thr Glu Cys Val Arg Val Asp Lys Asp Cys
        35                  40                  45

Ala Tyr Cys Thr Asp Glu Met Phe Arg Asp Arg Cys Asn Thr Gln
    50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Gly Thr Gln Ile Asp Thr Thr Leu
                85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415
```

```
His Val Asp Gly Thr His Val Cys Gln Leu Pro Glu Asp Gln Lys Gly
                420                 425                 430

Asn Ile His Leu Lys Pro Ser Phe Ser Asp Gly Leu Lys Met Asp Ala
            435                 440                 445

Gly Ile Ile Cys Asp Val Cys Thr Cys Glu Leu Gln Lys Glu Val Arg
        450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525

Gly Arg Tyr Glu Gly Gln Phe Cys Glu Tyr Asp Asn Phe Gln Cys Pro
530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
                645                 650                 655

Met Val Asp Glu Leu Lys Arg Ala Glu Glu Val Val Arg Cys Ser
            660                 665                 670

Phe Arg Asp Glu Asp Asp Cys Thr Tyr Ser Tyr Thr Met Glu Gly
        675                 680                 685

Asp Gly Ala Pro Gly Pro Asn Ser Thr Val Leu Val His Lys Lys Lys
690                 695                 700

Asp Cys Pro Pro Gly Ser Phe Trp Trp Leu Ile Pro Leu Leu Leu Leu
705                 710                 715                 720

Leu Leu Pro Leu Leu Ala Leu Leu Leu Leu Cys Trp Lys Tyr Cys
                725                 730                 735

Ala Cys Cys Lys Ala Cys Leu Ala Leu Leu Pro Cys Cys Asn Arg Gly
            740                 745                 750

His Met Val Gly Phe Lys Glu Asp His Tyr Met Leu Arg Glu Asn Leu
        755                 760                 765

Met Ala Ser Asp His Leu Asp Thr Pro Met Leu Arg Ser Gly Asn Leu
770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830
```

-continued

```
Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860

Gln Gln Thr Lys Phe Arg Gln Gln Pro Asn Ala Gly Lys Lys Gln Asp
865                 870                 875                 880

His Thr Ile Val Asp Thr Val Leu Met Ala Pro Arg Ser Ala Lys Pro
                885                 890                 895

Ala Leu Leu Lys Leu Thr Glu Lys Val Gln Glu Arg Ala Phe His
            900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Glu Gly Val Glu Leu Val Asp Val
    930                 935                 940

Arg Val Pro Leu Phe Ile Arg Pro Glu Asp Asp Glu Lys Gln Leu
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser  Val Ser Arg Gly Asp  Gln Val Ala
        995                 1000                1005

Arg Ile  Pro Val Ile Arg Arg  Val Leu Asp Gly Gly  Lys Ser Gln
    1010                1015                1020

Val Ser  Tyr Arg Thr Gln Asp  Gly Thr Ala Gln Gly  Asn Arg Asp
    1025                1030                1035

Tyr Ile  Pro Val Glu Gly Glu  Leu Leu Phe Gln Pro  Gly Glu Ala
    1040                1045                1050

Trp Lys  Glu Leu Gln Val Lys  Leu Leu Glu Leu Gln  Glu Val Asp
    1055                1060                1065

Ser Leu  Leu Arg Gly Arg Gln  Val Arg Arg Phe His  Val Gln Leu
    1070                1075                1080

Ser Asn  Pro Lys Phe Gly Ala  His Leu Gly Gln Pro  His Ser Thr
    1085                1090                1095

Thr Ile  Ile Ile Arg Asp Pro  Asp Glu Leu Asp Arg  Ser Phe Thr
    1100                1105                1110

Ser Gln  Met Leu Ser Ser Gln  Pro Pro Pro His Gly  Asp Leu Gly
    1115                1120                1125

Ala Pro  Gln Asn Pro Asn Ala  Lys Ala Ala Gly Ser  Arg Lys Ile
    1130                1135                1140

His Phe  Asn Trp Leu Pro Pro  Ser Gly Lys Pro Met  Gly Tyr Arg
    1145                1150                1155

Val Lys  Tyr Trp Ile Gln Gly  Asp Ser Glu Ser Glu  Ala His Leu
    1160                1165                1170

Leu Asp  Ser Lys Val Pro Ser  Val Glu Leu Thr Asn  Leu Tyr Pro
    1175                1180                1185

Tyr Cys  Asp Tyr Glu Met Lys  Val Cys Ala Tyr Gly  Ala Gln Gly
    1190                1195                1200

Glu Gly  Pro Tyr Ser Ser Leu  Val Ser Cys Arg Thr  His Gln Glu
    1205                1210                1215

Val Pro  Ser Glu Pro Gly Arg  Leu Ala Phe Asn Val  Val Ser Ser
    1220                1225                1230
```

-continued

```
Thr Val Thr Gln Leu Ser Trp Ala Glu Pro Ala Glu Thr Asn Gly
    1235                1240                1245

Glu Ile Thr Ala Tyr Glu Val Cys Tyr Gly Leu Val Asn Asp Asp
    1250                1255                1260

Asn Arg Pro Ile Gly Pro Met Lys Lys Val Leu Val Asp Asn Pro
    1265                1270                1275

Lys Asn Arg Met Leu Leu Ile Glu Asn Leu Arg Glu Ser Gln Pro
    1280                1285                1290

Tyr Arg Tyr Thr Val Lys Ala Arg Asn Gly Ala Gly Trp Gly Pro
    1295                1300                1305

Glu Arg Glu Ala Ile Ile Asn Leu Ala Thr Gln Pro Lys Arg Pro
    1310                1315                1320

Met Ser Ile Pro Ile Ile Pro Asp Ile Pro Ile Val Asp Ala Gln
    1325                1330                1335

Ser Gly Glu Asp Tyr Asp Ser Phe Leu Met Tyr Ser Asp Asp Val
    1340                1345                1350

Leu Arg Ser Pro Ser Gly Ser Gln Arg Pro Ser Val Ser Asp Asp
    1355                1360                1365

Thr Gly Cys Gly Trp Lys Phe Glu Pro Leu Leu Gly Glu Glu Leu
    1370                1375                1380

Asp Leu Arg Arg Val Thr Trp Arg Leu Pro Pro Glu Leu Ile Pro
    1385                1390                1395

Arg Leu Ser Ala Ser Ser Gly Arg Ser Ser Asp Ala Glu Ala Pro
    1400                1405                1410

His Gly Pro Pro Asp Asp Gly Gly Ala Gly Gly Lys Gly Gly Ser
    1415                1420                1425

Leu Pro Arg Ser Ala Thr Pro Gly Pro Pro Gly Glu His Leu Val
    1430                1435                1440

Asn Gly Arg Met Asp Phe Ala Phe Pro Gly Ser Thr Asn Ser Leu
    1445                1450                1455

His Arg Met Thr Thr Thr Ser Ala Ala Ala Tyr Gly Thr His Leu
    1460                1465                1470

Ser Pro His Val Pro His Arg Val Leu Ser Thr Ser Ser Thr Leu
    1475                1480                1485

Thr Arg Asp Tyr Asn Ser Leu Thr Arg Ser Glu His Ser His Ser
    1490                1495                1500

Thr Thr Leu Pro Arg Asp Tyr Ser Thr Leu Thr Ser Val Ser Ser
    1505                1510                1515

His Asp Ser Arg Leu Thr Ala Gly Val Pro Asp Thr Pro Thr Arg
    1520                1525                1530

Leu Val Phe Ser Ala Leu Gly Pro Thr Ser Leu Arg Val Ser Trp
    1535                1540                1545

Gln Glu Pro Arg Cys Glu Arg Pro Leu Gln Gly Tyr Ser Val Glu
    1550                1555                1560

Tyr Gln Leu Leu Asn Gly Gly Glu Leu His Arg Leu Asn Ile Pro
    1565                1570                1575

Asn Pro Ala Gln Thr Ser Val Val Val Glu Asp Leu Leu Pro Asn
    1580                1585                1590

His Ser Tyr Val Phe Arg Val Arg Ala Gln Ser Gln Glu Gly Trp
    1595                1600                1605

Gly Arg Glu Arg Glu Gly Val Ile Thr Ile Glu Ser Gln Val His
    1610                1615                1620
```

```
Pro Gln Ser Pro Leu Cys Pro Leu Pro Gly Ser Ala Phe Thr Leu
    1625                1630                1635

Ser Thr Pro Ser Ala Pro Gly Pro Leu Val Phe Thr Ala Leu Ser
    1640                1645                1650

Pro Asp Ser Leu Gln Leu Ser Trp Glu Arg Pro Arg Arg Pro Asn
    1655                1660                1665

Gly Asp Ile Val Gly Tyr Leu Val Thr Cys Glu Met Ala Gln Gly
    1670                1675                1680

Gly Gly Pro Ala Thr Ala Phe Arg Val Asp Gly Asp Ser Pro Glu
    1685                1690                1695

Ser Arg Leu Thr Val Pro Gly Leu Ser Glu Asn Val Pro Tyr Lys
    1700                1705                1710

Phe Lys Val Gln Ala Arg Thr Thr Glu Gly Phe Gly Pro Glu Arg
    1715                1720                1725

Glu Gly Ile Ile Thr Ile Glu Ser Gln Asp Gly Gly Pro Phe Pro
    1730                1735                1740

Gln Leu Gly Ser Arg Ala Gly Leu Phe Gln His Pro Leu Gln Ser
    1745                1750                1755

Glu Tyr Ser Ser Ile Thr Thr Thr His Thr Ser Ala Thr Glu Pro
    1760                1765                1770

Phe Leu Val Asp Gly Pro Thr Leu Gly Ala Gln His Leu Glu Ala
    1775                1780                1785

Gly Gly Leu Glu His His His His His His His His
    1790                1795                1800

<210> SEQ ID NO 18
<211> LENGTH: 787
<212> TYPE: PRT
<213> ORGANISM: Artificial Sequence
<220> FEATURE:
<223> OTHER INFORMATION: SEQ ID NO 18 BP230-g-C-His

<400> SEQUENCE: 18

Met Asp Cys Thr Phe Lys Pro Asp Phe Glu Met Thr Val Lys Glu Cys
1               5                   10                  15

Gln His Ser Gly Glu Leu Ser Ser Arg Asn Thr Gly His Leu His Pro
                20                  25                  30

Thr Pro Arg Ser Pro Leu Leu Arg Trp Thr Gln Glu Pro Gln Pro Leu
            35                  40                  45

Glu Glu Lys Trp Gln His Arg Val Val Glu Gln Ile Pro Lys Glu Val
        50                  55                  60

Gln Phe Gln Pro Pro Gly Ala Pro Leu Glu Lys Glu Lys Ser Gln Gln
65                  70                  75                  80

Cys Tyr Ser Glu Tyr Phe Ser Gln Thr Ser Thr Glu Leu Gln Ile Thr
                85                  90                  95

Phe Asp Glu Thr Asn Pro Ile Thr Arg Leu Ser Glu Ile Glu Lys Ile
                100                 105                 110

Arg Asp Gln Ala Leu Asn Asn Ser Arg Pro Pro Val Arg Tyr Gln Asp
            115                 120                 125

Asn Ala Cys Glu Met Glu Leu Val Lys Val Leu Thr Pro Leu Glu Ile
        130                 135                 140

Ala Lys Asn Lys Gln Tyr Asp Met His Thr Glu Val Thr Thr Leu Lys
145                 150                 155                 160

Gln Glu Lys Asn Pro Val Pro Ser Ala Glu Glu Trp Met Leu Glu Gly
                165                 170                 175
```

```
Cys Arg Ala Ser Gly Gly Leu Lys Lys Gly Asp Phe Leu Lys Lys Gly
            180                 185                 190

Leu Glu Pro Glu Thr Phe Gln Asn Phe Asp Gly Asp His Ala Cys Ser
        195                 200                 205

Val Arg Asp Asp Glu Phe Lys Phe Gln Gly Leu Arg His Thr Val Thr
210                 215                 220

Ala Arg Gln Leu Val Glu Ala Lys Leu Leu Asp Met Arg Thr Ile Glu
225                 230                 235                 240

Gln Leu Arg Leu Gly Leu Lys Thr Val Glu Val Gln Lys Thr Leu
            245                 250                 255

Asn Lys Phe Leu Thr Lys Ala Thr Ser Ile Ala Gly Leu Tyr Leu Glu
        260                 265                 270

Ser Thr Lys Glu Lys Ile Ser Phe Ala Ser Ala Ala Glu Arg Ile Ile
    275                 280                 285

Ile Asp Lys Met Val Ala Leu Ala Phe Leu Glu Ala Gln Ala Ala Thr
290                 295                 300

Gly Phe Ile Ile Asp Pro Ile Ser Gly Gln Thr Tyr Ser Val Glu Asp
305                 310                 315                 320

Ala Val Leu Lys Gly Val Val Asp Pro Glu Phe Arg Ile Arg Leu Leu
                325                 330                 335

Glu Ala Glu Lys Ala Ala Val Gly Tyr Ser Tyr Ser Ser Lys Thr Leu
            340                 345                 350

Ser Val Phe Gln Ala Met Glu Asn Arg Met Leu Asp Arg Gln Lys Gly
        355                 360                 365

Lys His Ile Leu Glu Ala Gln Ile Ala Ser Gly Gly Val Ile Asp Pro
    370                 375                 380

Val Arg Gly Ile Arg Val Pro Pro Glu Ile Ala Leu Gln Gln Gly Leu
385                 390                 395                 400

Leu Asn Asn Ala Ile Leu Gln Phe Leu His Glu Pro Ser Ser Asn Thr
                405                 410                 415

Arg Val Phe Pro Asn Pro Asn Asn Lys Gln Ala Leu Tyr Tyr Ser Glu
            420                 425                 430

Leu Leu Arg Met Cys Val Phe Asp Val Glu Ser Gln Cys Phe Leu Phe
        435                 440                 445

Pro Phe Gly Glu Arg Asn Ile Ser Asn Leu Asn Val Lys Lys Thr His
    450                 455                 460

Arg Ile Ser Val Val Asp Thr Lys Thr Gly Ser Glu Leu Thr Val Tyr
465                 470                 475                 480

Glu Ala Phe Gln Arg Asn Leu Ile Glu Lys Ser Ile Tyr Leu Glu Leu
                485                 490                 495

Ser Gly Gln Gln Tyr Gln Trp Lys Glu Ala Met Phe Phe Glu Ser Tyr
            500                 505                 510

Gly His Ser Ser His Met Leu Thr Asp Thr Lys Thr Gly Leu His Phe
        515                 520                 525

Asn Ile Asn Glu Ala Ile Glu Gln Gly Thr Ile Asp Lys Ala Leu Val
    530                 535                 540

Lys Lys Tyr Gln Glu Gly Leu Ile Thr Leu Thr Glu Leu Ala Asp Ser
545                 550                 555                 560

Leu Leu Ser Arg Leu Val Pro Lys Lys Asp Leu His Ser Pro Val Ala
                565                 570                 575

Gly Tyr Trp Leu Thr Ala Ser Gly Glu Arg Ile Ser Val Leu Lys Ala
            580                 585                 590
```

```
Ser Arg Arg Asn Leu Val Asp Arg Ile Thr Ala Leu Arg Cys Leu Glu
    595                 600                 605

Ala Gln Val Ser Thr Gly Gly Ile Ile Asp Pro Leu Thr Gly Lys Lys
    610                 615                 620

Tyr Arg Val Ala Glu Ala Leu His Arg Gly Leu Val Asp Glu Gly Phe
625                 630                 635                 640

Ala Gln Gln Leu Arg Gln Cys Glu Leu Val Ile Thr Gly Ile Gly His
                645                 650                 655

Pro Ile Thr Asn Lys Met Met Ser Val Val Glu Ala Val Asn Ala Asn
                660                 665                 670

Ile Ile Asn Lys Glu Met Gly Ile Arg Cys Leu Glu Phe Gln Tyr Leu
            675                 680                 685

Thr Gly Gly Leu Ile Glu Pro Gln Val His Ser Arg Leu Ser Ile Glu
        690                 695                 700

Glu Ala Leu Gln Val Gly Ile Ile Asp Val Leu Ile Ala Thr Lys Leu
705                 710                 715                 720

Lys Asp Gln Lys Ser Tyr Val Arg Asn Ile Ile Cys Pro Gln Thr Lys
                725                 730                 735

Arg Lys Leu Thr Tyr Lys Glu Ala Leu Glu Lys Ala Asp Phe Asp Phe
            740                 745                 750

His Thr Gly Leu Lys Leu Leu Glu Val Ser Glu Pro Leu Met Thr Gly
        755                 760                 765

Ile Ser Ser Leu Tyr Tyr Ser Ser Leu Leu Glu His His His His
    770                 775                 780

His His His
785
```

DIAGNOSTIC COINCUBATION ASSAY

The present invention relates to a method for the diagnosis of a disease comprising contacting a donor tissue section with a liquid capable of extracting an antibody from said donor tissue section and contacting said liquid with an acceptor material comprising an antigen, followed by detection of a complex comprising the antibody and the antigen, and a diagnostically useful carrier comprising a donor tissue section and an acceptor material comprising an antigen.

In most human beings, there exists, by default, a tolerance of all body components, i.e. they do not trigger the production of antibodies targeting their own tissue antigens. By contrast, disorders, referred to as autoimmune diseases, occur in which there is an apparent immunologic reaction of the host to his own tissues, often resulting in tissue injury.

The importance of an early and reliable diagnosis of autoimmune diseases cannot be overemphasized. Many autoimmune disorders cannot be cured, but therapies are available that may be used to significantly ameliorate their symptoms, often enabling patients to lead a normal life. The earlier the diagnosis, the better the chances to exploit the spectrum of therapies, such as administration of immunosuppressive drugs or a strict diet devoid of immunogenic antigens, to the full benefit of the patient.

The diagnosis of an autoimmune disease is frequently based on the output of a method for the detection of autoantibodies in a liquid sample comprising antibodies. Most frequently, blood serum routinely obtained from patients is used. In other cases, other liquids are used such as cerebrospinal fluid (CSF), in particular for the detection of autoantibodies associated with neurological symptoms.

Coeliac disease (CD) is a special example of an autoimmune disease. It is triggered by gluten which activates an immune reaction against the CD autoantigen, i.e. tissue transglutaminase (TTG), in genetically predisposed subjects. Following the finding that the presence of antibodies to gliadin and/or TTG is associated with CD it could be established that CD is not a rare, but a frequent condition with an expected prevalence higher than 1% in the worldwide population. A spectrum of diseases related to gluten sensitivity exists, including Non Coeliac Gluten sensitivity (NCGS) characterized by intestinal symptoms related to the ingestion of gluten-containing food, and in the case of a number of patients it remains difficult to thoroughly distinguish between them.

A pathologist with significant experience is required to examine tissue sections made from a bioptate as a basis for a reliable diagnosis. In many cases, such examination is inconclusive as characteristic features cannot be observed. However, the pathologist may not have at his disposal a serum sample from the patient to complement the histological analysis, or the concentration of antibodies in serum samples comprising peripheral blood may be insufficient.

In such a case, chances are significant that the patient will be misdiagnosed. False negative results may cause the patient to be denied adequate treatment, resulting in an increased risk of secondary disorders, among them cancers such as intestinal lymphoma, and a poor life quality.

Therefore, a problem underlying the present invention is to provide a method for diagnosing an autoimmune disease that may be used to corroborate an inconclusive histological examination of diseased tissue. Another problem is to provide an improved test having an increased sensitivity and reducing the likelihood of false negative results.

Not in the least a problem underlying the present invention is to provide an assay that may be run in the absence of serum samples and allows a pathologist to corroborate a diagnosis based on an inconclusive histological examination.

The problem underlying the present invention is solved by the subject-matter of the attached independent and dependent claims.

In a first aspect, the problem underlying the present invention is solved by a method for the diagnosis of a disease comprising contacting a donor tissue section with a liquid capable of extracting an antibody from said donor tissue section and contacting said liquid with an acceptor material comprising an antigen, optionally two or more antigens, followed by detection of a complex comprising the antibody and the antigen.

In a preferred embodiment, the donor tissue section and the acceptor material comprising an antigen are co-incubated in the liquid.

In a second aspect, the problem is solved by a diagnostically useful carrier comprising a donor tissue section and an acceptor material comprising an antigen, wherein the carrier is configured such that the donor tissue section and the acceptor material comprising an antigen may be co-incubated in a liquid capable of extracting an antibody from said donor tissue section and allowing the transport of the antibody to the acceptor material.

In a preferred embodiment, the donor tissue section and the acceptor material comprising an antigen are coated on the surface of the carrier and are preferably spatially separate.

In a preferred embodiment, the donor tissue section and the acceptor material comprising an antigen are on spatially separate biochips.

In a preferred embodiment, the carrier is configured such that a liquid capable of extracting an antibody from said donor tissue section may be placed on the surface of the carrier such that an antibody may be extracted from the donor tissue section and diffuse, via the liquid, to the acceptor material comprising an antigen.

In a preferred embodiment, the carrier comprises a first part having a surface coated with the donor tissue section and a second part having a surface coated with the acceptor material, wherein the first and the second part are separate and the carrier is configured such that the first and the second part may be contacted, preferably assembled such that the surface of either the first or the second part faces downwards on the surface of the other one of the first and the second part such that a drop of liquid may be placed between the surfaces of the first part and the second part to allow diffusion of any antibodies from the donor tissue section to the acceptor material.

In a preferred embodiment, the donor tissue section has been obtained from a patient to be diagnosed.

In a preferred embodiment, the acceptor material comprising an antigen is a tissue sample comprising the antigen, preferably in the form of a native polypeptide, a cell producing said antigen, or an isolated polypeptide.

In a preferred embodiment, the donor tissue section is a frozen tissue section.

In a preferred embodiment, the disease is a gastroenteropathy, preferably an inflammatory or autoimmune gastrointestinal disease, more preferably coeliac disease, the donor tissue section is a gastrointestinal, preferably duodenal tissue, and the antigen is tissue transglutaminase or deamidated gliadin or a variant thereof, preferably an oligomer of deamidated gliadin or a variant thereof.

In a preferred embodiment, the disease is pemphigus and/or pemphigoid, preferably bullous pemphigoid, the donor tissue section is diseased skin tissue, and the acceptor material comprises one or more antigens from the group comprising Dsg1, Dsg3, NC16A, BP180, BP 230, LAMA3 (SEQ ID NO 14), Laminin332, which is preferably a composition comprising polypeptides comprising LAMA3 (SEQ ID NO14), LAMB5 (SEQ ID NO 15), and LAMC2 (SEQ ID NO 16) and, beta4 integrin (SEQ ID NO 17) and collagen type VII and a variant thereof, optionally in the form of a tissue, preferably selected from the group comprising primate esophagus, human salt split skin and rat urinary bladder.

In a preferred embodiment, the disease is Goodpasture syndrome or SLE, the donor tissue section is diseased kidney tissue, and the acceptor material comprising the antigen is or is derived from a material selected from the group comprising antiglomerular basement membrane, dsDNS, human epithelial cells (HEp-2), pLA2R and THSD7A and a variant thereof.

In a preferred embodiment, the disease is Crohn's disease, the donor tissue section is diseased intestinal tissue, and the acceptor material comprising the antigen is selected from the group comprising healthy pancreas tissue, CUZD1 and GP2 and a variant thereof, the latter two preferably in the form of a cell expressing CUZD1 and/or GP2 and a variant thereof.

In a preferred embodiment, the disease is Grave's and/or Hashimoto's disease, the donor tissue section is derived from thyroid gland, and the acceptor material comprising the antigen is or is derived from healthy thyroid gland tissue.

In a preferred embodiment, the disease is myositis, the donor tissue section is muscle or skin, preferably muscle tissue, and the acceptor material comprising the antigen is MUP-44 or a variant thereof.

The present invention is based on the inventors' surprising finding that autoantibodies may be detected in tissue sections. For example, this holds true for antibodies associated with CD.

Without wishing to be bound to any theory, the inventors hypothesize that autoantibodies accumulate in diseased tissues and organs and that their transfer to the patient's blood is incomplete and insufficient for a reliable analysis based on serology.

According to the present invention, a donor tissue section is provided. This is a piece of tissue obtained from a patient suffering from or suspected of suffering from a disease to be diagnosed. In a preferred embodiment, the donor tissue section is frozen, preferably by immersion in liquid nitrogen or melting isopentane. The tissue section may preferably have a thickness of 1 to 100, preferably 4 to 50 µm. The donor tissue section has preferably not been treated with any reagents or exposed to conditions substantially altering the antibodies present in the donor tissue section.

According to the present invention, the donor tissue section is contacted with a liquid capable of extracting an antibody from said donor tissue section. This is any liquid that, upon exposure to the donor tissue section, may take up antibodies present in the donor tissue section, conserves their chemical composition, structure or binding properties such as the ability to bind specifically to an antigen, and allows their passage to the acceptor material comprising an antigen. Preferably, the liquid is an aqueous liquid comprising a physiological buffer, more preferably at pH 5 to 9, more preferably 6 to 8, most preferably 6.2 to 7.8. In a most preferred embodiment, the liquid is PBS pH 7.4.

In a preferred embodiment, the term "binding specifically", as used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7.4.

It is preferred that the liquid capable of extracting the antibody comprises a detergent that helps dissociating any antibodies from tissue whilst conserving their chemical composition, structure or binding properties, in particular the ability to specifically bind to an antigen, and is preferably Tween. In a preferred embodiment, the liquid comprises 0.1 to 10%, preferably 0.5 to 5%, more preferably 1 to 4%, most preferably 1.5 to 2.5% of a detergent.

According to the present invention, the donor tissue section is contacted with a liquid capable of extracting an antibody from said donor tissue section, and said liquid is contacted with an acceptor material comprising an antigen. The acceptor material comprises the antigen in a state and conformation that allows for the specific binding of an antibody. The acceptor material may be selected from the group comprising tissue containing an antigen, preferably in the form of a native polypeptide, more preferably an endogenous, native polypeptide, a cell producing an antigen, preferably a recombinant cell overexpressing an antigen, and an isolated polypeptide. The cell may be intact or a lysed cell.

In a preferred embodiment, the donor tissue section and the acceptor material comprising an antigen are co-incubated in the liquid, i.e. both the donor tissue section and the acceptor material are contacted with the liquid at the same time as the antibody is extracted from the donor tissue section and transported to the acceptor material. This co-incubation step is carried out for at least 10, 20, 30, 60 minutes, 2, 3, 4, 6, 8, 10 or 12 hours.

Alternatively, the donor tissue section and the liquid may be contacted first, followed by separation of the donor tissue section and the liquid and contacting of the liquid and the acceptor material comprising an antigen. The liquid may be stored, frozen and/or concentrated prior to contacting it with the acceptor material comprising an antigen. Both contacting steps may be carried out for at least 10, 20, 30, 60 minutes, 2, 3, 4, 6, 8, 10 or 12 hours.

Subsequently, the acceptor material is separated from the liquid capable of extracting an antibody and/or the donor tissue section, for example by separating the first or second part of the carrier or by removing the liquid, for example by way of aspiration. The acceptor material may be washed at least once using a washing buffer. Fresh liquid capable of extracting the antibody may be used as washing buffer, preferably comprising a smaller concentration of detergent such as 10% of the concentration used in the incubation step or no detergent at all.

Subsequently, any complex comprising the antibody and the antigen may be detected. In a preferred embodiment, the complex is detected using a method selected from the group comprising immunodiffusion techniques, immunoelectrophoretic techniques, light scattering immunoassays, agglutination techniques, labeled immunoassays such as those from the group comprising radiolabeled immunoassays, enzyme immunoassays such as ELISA, chemiluminscence immunoassays, and immunofluorescence techniques. The person skilled in the art is familiar with these methods.

The invention relates to a diagnostically useful carrier, which is preferably a solid, artificial carrier for contacting a donor tissue section and/or, preferably and an acceptor material comprising an antigen, which donor tissue section and/or acceptor material is coated on the surface of said carrier, with a liquid capable of extracting an antibody from the donor tissue section. Preferably, the donor tissue section and the acceptor material are surrounded by a hydrophobic surface to fix the position of the liquid capable of extracting an antibody. In a preferred embodiment, the solid carrier comprises two or more separate parts, one comprising the donor tissue section and one comprising the acceptor material, each separate part preferably selected from the group comprising a bead, a microtiter plate, a glass surface, a biochip and a membrane, most preferably a biochip.

In a preferred embodiment, the term "biochip", as used herein, refers to a planar, thin slide having a thickness of 0.01 to 1 mm, preferably 0.02 to 0.5 mm, more preferably 0.05 to 0.4 mm. They are preferably made of glass or plastic. They are coated with a biological agent such as a donor tissue section or an acceptor material comprising an antigen.

In a preferred embodiment, the diagnostically useful carrier may be coated with donor tissue section and coated with the acceptor material comprising an antigen. The donor tissue section and the acceptor material, both preferably on a biochip, may be sized and placed in close proximity such that a drop of liquid capable of extracting the antibody, preferably having a volume of 10 to 80, preferably 20 to 60 µl, may be placed in contact with both the donor tissue section and the acceptor material at the same time for the incubation step. Coated donor tissue section and coated acceptor material comprising an antigen on the diagnostically useful carrier are preferably spatially separated, in particular such that one may be added or removed from the diagnostically useful carrier independent of the other.

In a preferred embodiment, the contacting step may be carried out as follows: a drop of liquid is placed on a surface and the diagnostically carrier is contacted with said drop such that the donor tissue section and the acceptor material, both on the same side of the diagnostically useful carrier, face downward when touching the drop sitting on the carrier. Owing to their hydrophilic natures, the surface, the donor tissue section and the acceptor material adhere to and fix the liquid drop for the entirety of the coincubation. The extraction and passage of antibodies through the liquid from the donor tissue section to the acceptor material may be supported by gently rocking the diagnostically useful carrier together with the surface. Devices for carrying out the incubation are described in US2010/0124750.

FIG. 1 illustrates this way of carrying out the method according to the invention: a diagnostically relevant carrier (1) comprising a donor tissue section (2) comprising an antibody (3) and, in close proximity an acceptor material (4) comprising an antigen (5) is placed on top of a hydrophilic surface (6) on which a drop of liquid capable of extracting antibodies (7) is located. The diagnostically relevant carrier (1) is place on top of the hydrophilic surface (6) such that the antibodies (3) may passage from the donor tissue section (2) to the antigen (5) via the liquid and form a complex. Subsequently, the hydrophilic surface and the diagnostically useful carrier are separated. A complex comprising the antigen and the antibody, if present, may be detected.

In another preferred embodiment, the carrier comprises a first part having a surface coated with the donor tissue section and a second part having a surface coated with the acceptor material comprising an antigen, wherein the first and the second part are separate and the carrier is configured such that the first and the second part may be contacted, preferably assembled such that the surface of either the first or the second part faces downwards on the surface of the other one of the first and the second part such that a drop of liquid may be placed between the surfaces of the first part and the second part to allow diffusion of any antibodies from the donor tissue section to the acceptor material. FIG. 2 illustrates this way of carrying out the method according to the invention.

In another preferred embodiment, the first part of the carrier is a bead coated with the acceptor material comprising an antigen, and this is contacted with the donor tissue section. The latter is preferably coated on the surface of a second part of the carrier, but may also be non-immobilized, for example floating in solution rather than being coated.

The acceptor material may comprise or consist of a polypeptide antigen, for example in a tissue, cell or in purified form represented by exact sequences referred to in this application explicitly, for example by function, name, sequence or accession number, or implicitly, but also including variants of such polypeptides.

In a preferred embodiment, the term "variant", as used herein, may refer to at least one fragment of the full length sequence referred to, more specifically one or more amino acid which are, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids. Variants may include full-length sequences or fragments that are at least 40, 50, 60, 70, 75, 80, 85, 90, 92, 94, 95, 96, 97, 98 or 99% identical to the reference amino acid sequence referred to or the corresponding fragment of said reference amino acid sequences.

Any variants thereof may, in addition, comprise chemical modifications, for example isotopic labels or covalent modifications such as glycosylation, phosphorylation, acetylation, decarboxylation, citrullination, methylation, hydroxylation and the like.

The variant of the polypeptide, preferably comprising an antigen, has biological activity. In a preferred embodiment, such biological activity is the ability to bind specifically to the antibodies, preferably autoantibodies of interest found in patients suffering from the respective disease. For example, the biological activity of a variant of an antigen such as deamidated gliadin may be the ability to bind specifically to an antibody from a patient to deamidated gliadin, the presence of which suggests that the patient suffers from a disease, such as a patient suffering from CD in the case of a deamidated gliadin variant.

The polypeptide or a variant thereof may be provided in any form and at any degree of purification, from liquid samples, tissues or cells comprising said polypeptide in an endogenous form, more preferably cells overexpressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process. In a preferred embodiment, a polypeptide is pure if at least 60, 70, 80, 90, 95 or 99 percent of the polypeptide in the respective sample consists of said polypeptide as judged by SDS PAGE followed by Coomassie blue staining and visual inspection. A recombinant polypeptide may comprise two or more copies of an antigen, preferably fused to one another.

If the antigen is provided in the form of tissue, it is preferred that the tissue is mammalian tissue, for example human, rat, primate, donkey, mouse, goat, horse, sheep, pig or cow.

According to the present invention, a method for the diagnosis of a disease is provided. In a preferred embodiment, the term "diagnosis", as used herein, refers to any kind of procedure aiming to obtain information instrumental in the assessment of whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of immunosuppressive drugs. In other words, the term "diagnosis" comprises not only diagnosing, but also prognosticating and/or monitoring the course of a disease or disorder.

In many cases the mere detection, in other words determining whether or not detectable levels of the antibody are present in the sample, is instrumental for the diagnosis as it indicates an increased likelihood that the patient suffers from a disease. In a preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 0.1, preferably 0.2, 0.5, 1, 2, 5, 10, 20, 25, 50, 100, 200, 500, 1000, 10000 or 100000 times higher than the concentration found in the average healthy subject.

The person skilled in the art will appreciate that a clinician does usually not conclude whether or not the patient suffers or is likely to suffer from a disease, condition or disorders solely on the basis of a single diagnostic parameter, but also other aspects, for example the presence of other autoantibodies, markers, blood parameters, clinical assessment of the patient's symptoms or the results of medical imaging or other non-invasive methods such as polysomnography, to arrive at a conclusive diagnosis. (See Baenkler H. W. (2012), General aspects of autoimmune diagnostics, in Renz, H., Autoimmune diagnostics, 2012, de Gruyter, page 3.) The value of a diagnostic agent or method may also reside the possibility to rule out one disease, thus allowing for the indirect diagnosis of another.

The term "diagnosis" may also refer to a method or agent used to distinguish between two or more conditions associated with similar or identical symptoms. The term "diagnosis" may also refer to a method or agent used to choose the most promising treatment regime for a patient. In other words, the method or agent may relate to selecting a treatment regimen for a subject.

In a preferred embodiment, the antibody to be detected is an autoantibody. In another preferred embodiment, the antibody to be detected is an IgG or IgA class antibody, preferably an IgA class antibody.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. For example, if the amount of complex is found to increase, this suggests that the disorder is progressing, likely to manifest in the future and/or that any treatment attempted is unsuccessful.

The inventive teachings provide a kit, preferably for diagnosing a disease, comprising the diagnostically useful carrier according to the present invention. The diagnostically useful carrier may initially comprise the acceptor material comprising an antigen only, and is configured such that the end customer may add the donor tissue section prior to carrying out the inventive method. In addition, said kit may comprise instructions detailing how to use the kit and a means for contacting the inventive polypeptide with a bodily fluid sample from a subject, preferably a human subject. Furthermore, the kit may comprise a positive control, for example a batch of antibody or recombinant antibody known to bind to the inventive polypeptide and a negative control, for example a protein having no detectable affinity to the inventive polypeptide such as bovine serum albumin. Finally, such a kit may comprise a standard solution of the antibody or antigen for preparing a calibration curve.

In a preferred embodiment, the kit comprises a means for detecting an antibody binding to the antigen in the acceptor material, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the antibody, preferably a secondary antibody specific for human antibodies.

In a preferred embodiment, the disease to be diagnosed is a gastroenteropathy, preferably an inflammatory or autoimmune gastrointestinal disease, more preferably coeliac disease, the donor tissue section is a gastrointestinal, preferably duodenal tissue, and the antigen is selected from the group comprising tissue transglutaminase (Uniprot data base: P21980, referring to the version online at the priority data, as all data base codes cited throughout this document) or a variant thereof or a gliadin variant selected from the group comprising SEQ ID NO 1, SEQ ID NO3, SEQ ID NO4, SEQ ID NO5 and variants thereof, preferably more than one copy thereof fused, for example SEQ ID NO 2. The method or carrier may be used to diagnose NCGS, preferably to distinguish between gastroenteropathies related to gluten sensitivity, more preferably CD and NCGS. The antibody to be detected is preferably an IgA class antibody to TTG or deamidated gliadin, more preferably to deamidated gliadin.

In another preferred embodiment, the disease to be diagnosed is pemphigus and/or pemphigoid, preferably bullous pemphigoid, the donor tissue section is diseased skin tissue, and the antigen is selected from the group comprising Dsg1 (Uni prot data base code Q02413), Dsg3 (Uni prot data base code P32926), NC16A (SEQ ID NO 6), optionally in the form of a fusion comprising two or more copies of such as SEQ ID NO 7, BP180 (Uni prot data base code Q9UMD9), BP 230 (SEQ ID NO 8) and collagen type VII (Uni prot data base code Q02388) or a variant thereof.

In another preferred embodiment, the disease to be diagnosed is Goodpasture syndrome or SLE, the donor tissue section is diseased kidney tissue, and the acceptor material comprising the antigen is selected from the group comprising antiglomerular basement membrane, dsDNS, human epithelial cells (HEp-2), pLA2R (SEQ ID NO 9) and THSD7A (SEQ ID NO 10) or a variant thereof.

In another preferred embodiment, the disease to be diagnosed is Crohn's disease, the donor tissue section is diseased intestinal tissue, and the antigen is selected from the group comprising CUZD1 (SEQ ID NO 11) and GP2 (SEQ ID NO 12) or a variant thereof.

In another preferred embodiment, the disease to be diagnosed is Grave's and/or Hashimoto's disease, the donor tissue section is derived from thyroid gland, and the antigen is or is derived from healthy thyroid gland tissue.

In another preferred embodiment, the disease to be diagnosed is myositis, the donor tissue section is muscle or skin, preferably muscle tissue, and the antigen is or is derived from MUP-44 (SEQ ID NO 13) or a variant thereof.

The present invention is further illustrated by the non-limiting additional figures and the following non-limiting examples from which further features, embodiments, aspects and advantages of the present invention may be taken.

EXAMPLE 1

Figure 1:
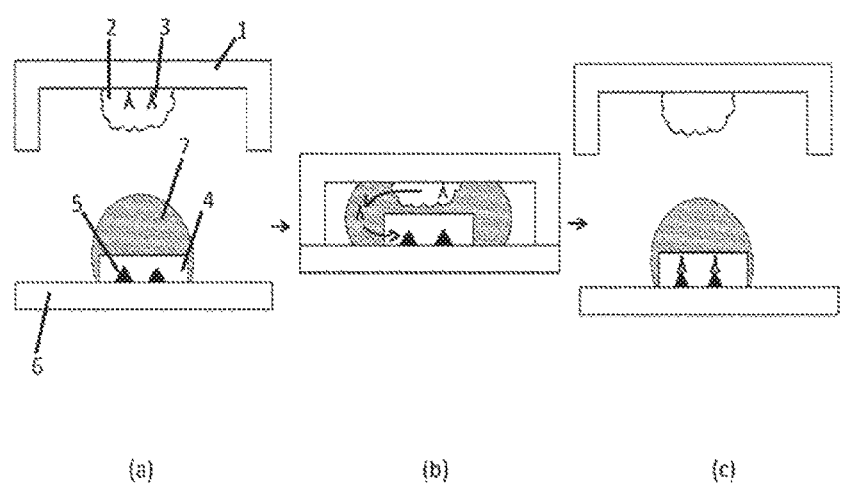
FIG. 1 shows an embodiment involving a donor tissue section on a carrier, and an acceptor material on a hydrophilic surface.

Manufacture of the Diagnostically Useful Carrier and its Use According to the Present Invention A biochip coated with a cryosection (4 µm) of the bioptate (frozen in liquid nitrogen) as tissue donor section was placed beside a biochip coated with dots of purified recombinant antigen GAF-3X (EUROPLUS) (SEQ ID NO 2) as acceptor material comprising an antigen within one reaction field on a microscopic slide. This was repeated with all bioptates obtained from other patients.

The microscopic slide comprising both biochips were incubated with a drop of PBST buffer (PBS with 2% (v/v) Tween-20, pH 7.4) placed in contact with both the bioptate and the antigen at 4° C. overnight. This way, antibodies eluted from the tissue could diffuse in the buffer and antibodies binding to deamidated gliadin could bind to the adjacent GAF-3X antigen dots and be detected. The next day, the biochips were washed using PBST (PBS with 0.2% (v/v) Tween-20, pH 7.4) for 5 minutes. Subsequently, the biochips were incubated with FITC-conjugated anti-human IgA antibodies (Euroimmun AG) for 30 minutes and again washed for 5 minutes. Finally, the slides were analyzed using a fluorescence microscope (EUROStar).

Samples

The analyzed cohort comprised 37 patients with coeliac disease diagnosed on the basis of histological examination of the bioptates by an experienced clinician and 35 healthy control persons. Duodenal biopsies from the Bulbus duodeni (36 CD patients, 34 control individuals) were obtained. Serum samples were available for all individuals. Samples were blinded for incubation and microscopic analyses and decoded for final evaluation of the data.

Serum samples were additionally tested using the commercial Anti-GAF-3X-IIFT (IgA) and Anti-GAF-3X ELISA (IgA) according to manufacturer's instructions (EUROIMMUN AG, Germany, products FV 3011-#A and EV 3011-9601A, respectively).

Serological Analyses of 81 Serum Samples (not According to the Present Invention)

Using the immunofluorescence test, 28 samples were IgA anti-GAF-3X antibody positive among 37 tested CD patients, yielding a sensitivity of 76%. Of 35 control samples none was positive in the Anti-GAF-3X-IIFT (IgA). Therefore, the IIFT (IgA) reached a specificity of 100%.

Enhanced Sensitivity for IgA Detection Obtained Using the Method According to the Present Invention Using Bulbus doudeni biopsies in the method according to the present invention, 32 out of 36 CD patients (samples of whom were available) were tested positive for IgA anti-GAF-3X antibodies. Among these 32 patients, five were tested negative in both the ELISA and the IIFT. 34 bulbus biopsies of control individuals were further tested of which only one exhibited anti-GAF-3X antibodies of class IgA.

In summary, the Co-Incubation test with Bulbus duodeni biopsies was 89% sensitive for IgA anti-GAF-3X, thereby reaching a specificity of 97%.

The results show that antibodies binding to deamidated gliadin are present within the small intestinal mucosa and may be detected using the inventive method in tissue section from patients serum samples of whom are negative. As a result, the number of false negative results may be reduced.

EXAMPLE 2

Bullous pemphigoid (BP) and pemphigus vulgaris (PV) are associated with circulating autoantibodies against BP180, BP230 and desmoglein (Dsg1, Dsg3).

Antibodies against BP 180 and/or BP230 give a serological indication of bullous pemphigoid. It may also be the rarely found lichen planus pemphigoides or the similarly unfrequent mucous membrane (only BP180) or cicatricial pemphigoid (only BP180), which predominantly occurs in elderly people. In pregnant women, pemphigoid gestationis should be taken into account.

Antibodies against Desmoglein 1 indicate the disease Pemphigus folicaceus, while antibodies against Desmoglein 3 (sometimes additionally anti Desmoglein 1) appear in Pemphigus vulgaris.

Direct immunofluorescence (DIF) on biopsies shows staining of desmosomes in pemphigus diseases and of the epidermal basement membrane in pemphigoid diseases. For this purpose, tissue sections from biopsy material of patients are made, incubated with a fluorescent dye-labeled anti-human monoclonal antibody and then evaluated using a fluorescence microscope.

Serological differentiation then has to be carried out with monospecific tests, e.g. by indirect immunofluorescence (IIF) with recombinant HEK cells (expressing specific antigens), and antigen preparations (EUROPLUS®). This step is important to determine the diagnosis, since several target antigens are suitable for the fluorescence of the basal membrane and the desmosomes respectively. BIOCHIP™-Mosaics, consisting of several small glass chips coated with tissue, cell substrates or preparations of small antigen dots (EUROPLUS®) in one reaction field are consecutively incubated with patient's sera and fluorescently labelled antisera. Afterwards they are microscopically evaluated according to the manufacturer's instructions.

The aim of this study was the monospecific determination of antibodies eluted from tissue by co-incubation of biopsies and cell preparations or antigen dots of recombinant proteins in IIF, contrary to conventional IIFT, which is performed with serum samples. This allows the search test (usually DIF) and confirmation test (usually IIFT) to be performed in one step.

Figure 2:
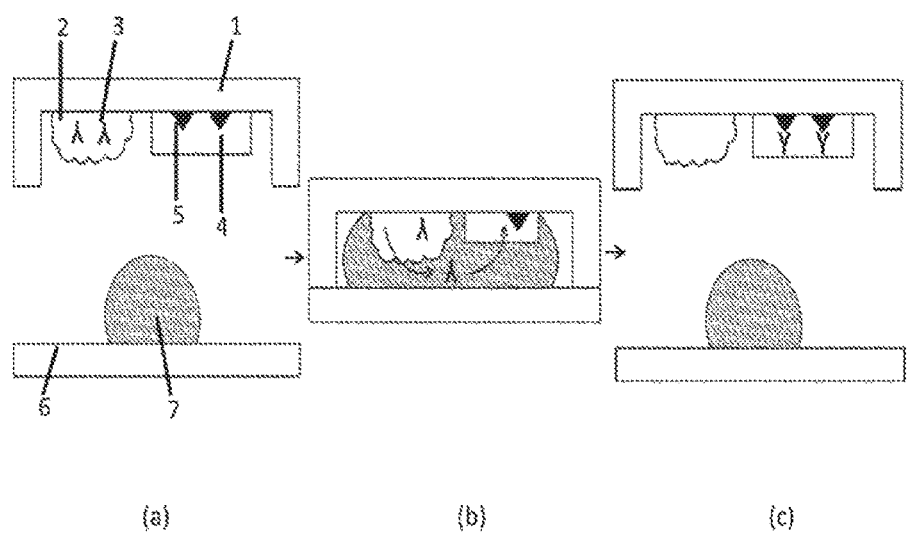
FIG. 2 shows another embodiment involving a donor tissue section on a first part of a carrier, and an acceptor material on a second part of a carrier.
Figure 3:
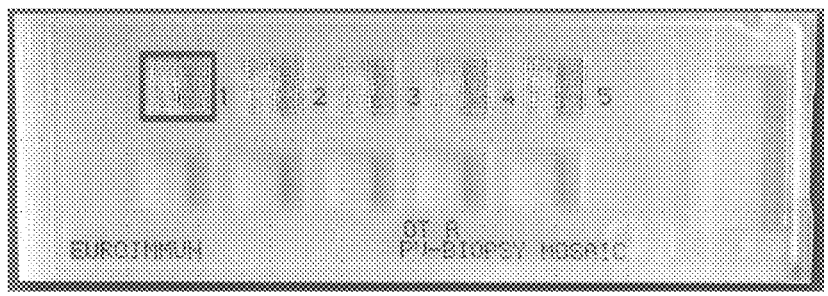
FIG. 3 shows a slide comprising BIOCHIP mosaics as used in the present invention.
Figure 4:
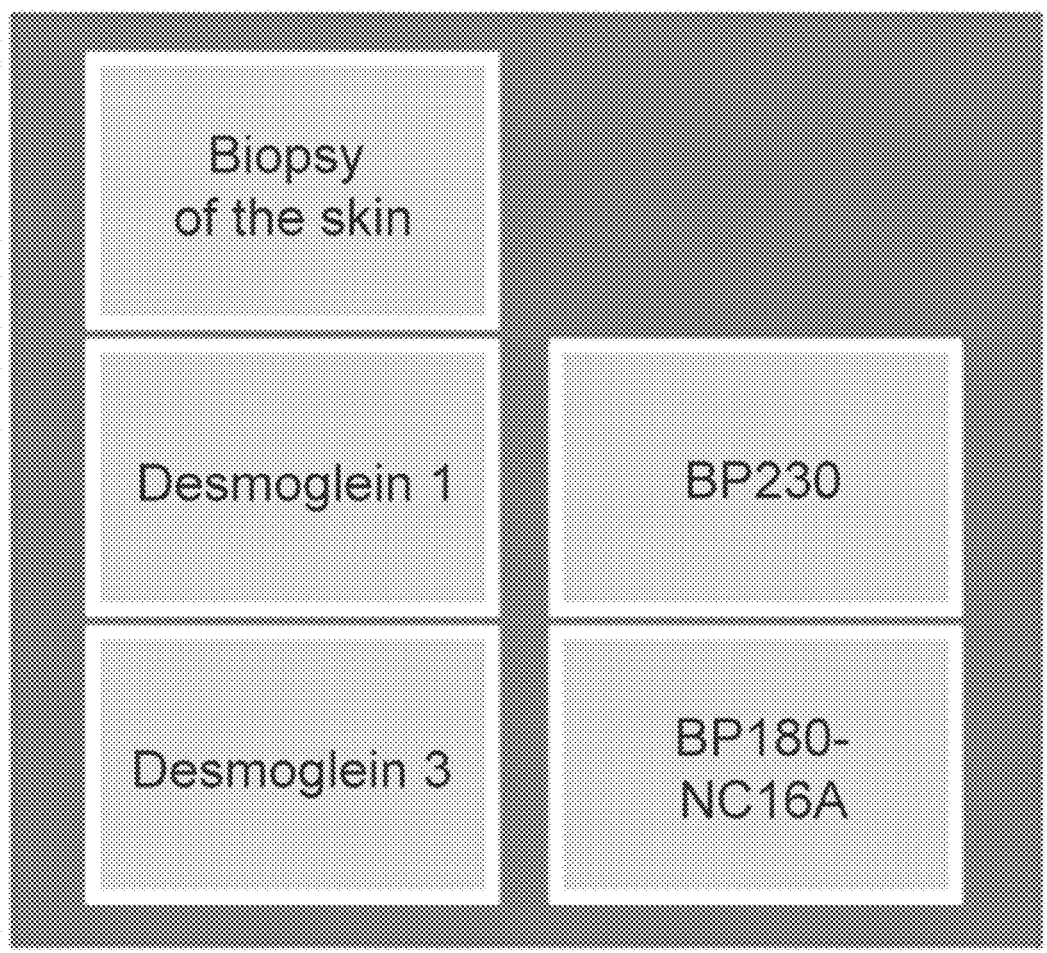
FIG. 4 shows the locations of the skin biopsy sample as well as various acceptor materials, more specifically HEK293 cells expressing Desmogl-ein 1, BP230gc (SEQ ID NO 18), Desmoglein 3 and BP180-NC16A, respectively.

Frozen sections from a biopsy of one PV and two BP patients, respectively, were combined to BIOCHIP™-Mosaics on one slide with HEK293 cells transfected with Desmoglein 1 (EUROIMMUN, substrate FD 1495-50; DSG1), Desmoglein 3 (EUROIMMUN substrate FD 1496-50; DSG3), BP230 (EUROIMMUN substrate FD 1502-56; BP230gC (SEQ ID NO 18)) or anti-BP180-NC16A-4X (EUROIMMUN substrate FD 1502-52; BP180-NC16A-4X) (FIGS. 1 and 2). The tissue slices, acetone or formaldehyde fixed recombinant cell preparations or antigen preparations (EUROPLUS®) are used as antigenic substrates. The technology described in EP Patent 0 117 262 was used. Briefly, very thin glass plates chemically coated with spontaneously reacting aldehyde groups were covered with the antigens. Cell cultures directly grew on the glass plates. Free amino groups of the tissue slices, particularly the hydroxyl lysine of collagen, covalently adhered to the carrier material so that the tissue could not be removed by the following incubations with liquid reagents. The glass plates were industrially cut in very small glass chips with an edge length of 1-2 mm. Glass chips coated with different antigens can be combined in one reaction field of a slide to obtain a so called BIOCHIP-Mosaic™.

The individual mosaics were incubated with 30 µl PBS-Tween20 (2%) for 15 hours at 4° C. Bound antibodies were visualised by a FITC-labeled anti-human IgG antibody (EUROIMMUN, product no. AF 102, FITC-labelled anti-human-IgG (goat)). The incubation is carried out for 30 min. at room temperature (20-25° C.). The slides were washed with PBS-Tween20 (0.2%) for 5 min. after both incubation steps. Then they were covered and evaluated under a fluorescence microscope (Axio Scope A1, Zeiss, Jena, Germany, article no. 490035-9100-000).

Figure 5:
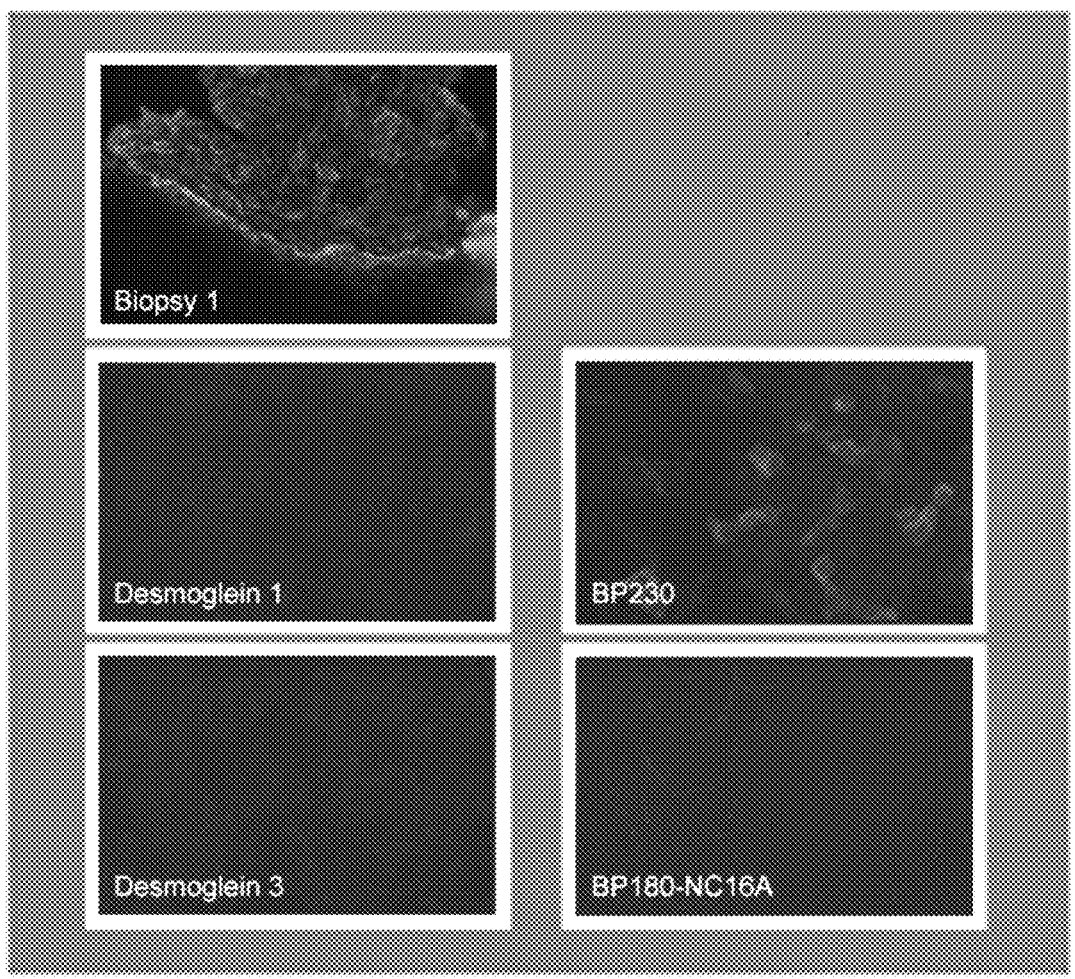
FIG. 5 shows the immunofluorescence analysis of a positive biopsy sample, wherein autoantibodies to BP230 are detectable.
Figure 6:
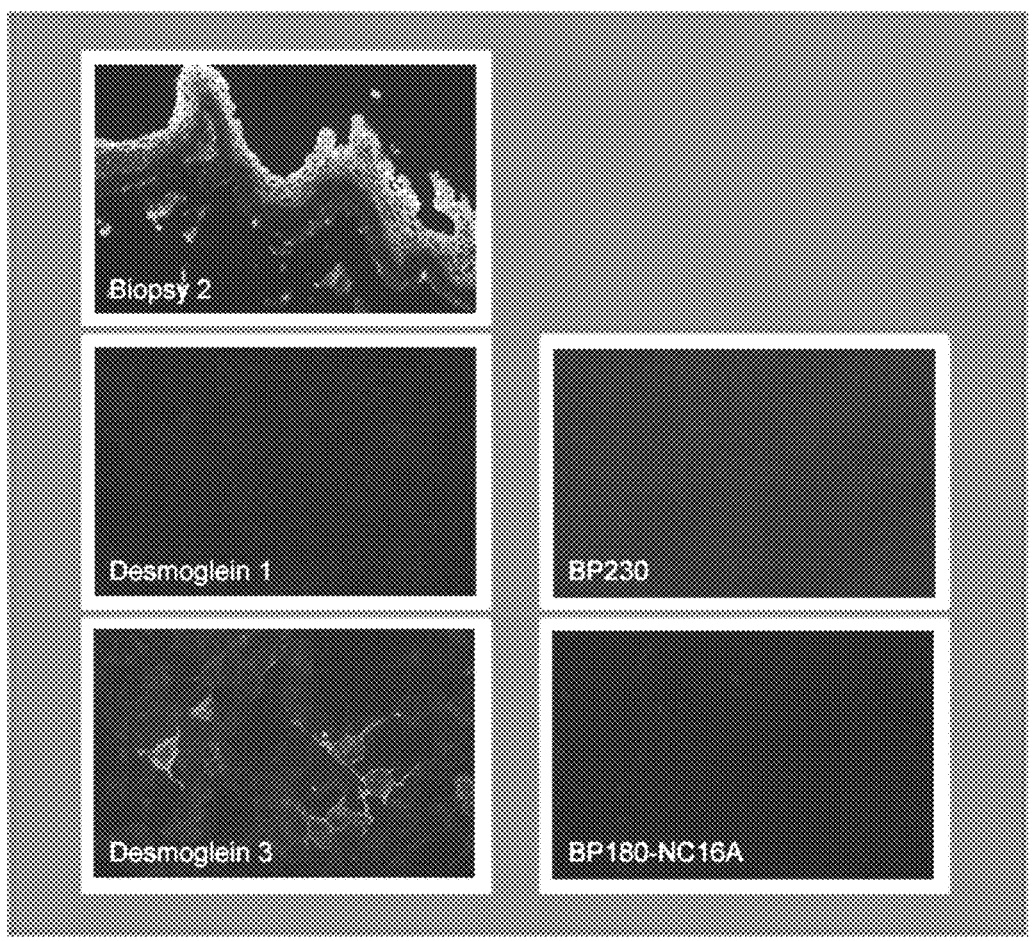
FIG. 6 shows the immunofluorescence analysis of a positive biopsy sample, wherein autoantibodies to Desmoglein 3 are detectable.

Co-incubation of the PV biopsy showed parallel reactivity to desmosomes and Dsg3 (see FIG. 6 for an exemplary image), while co-incubation of the two BP biopsies resulted in staining of the epidermal basement membrane and BP180 and BP230 antigens (see FIG. 5 for an exemplary image). In contrast to the conventional IIFT, in which antibodies are detected in the serum of the patient, antibodies are detected which are present in residues of body fluids within the biopsy using the co-incubation technology.

---

The invention claimed is:

1. A method for the diagnosis of an autoimmune disease, comprising:
   contacting a solid donor tissue section with a liquid capable of extracting an antibody from said donor tissue section and contacting said liquid with an acceptor material comprising an antigen in close proximity to said tissue section,
   followed by detection of a complex comprising the antibody and the antigen,
   wherein the donor tissue section and the acceptor material comprising an antigen are co-incubated in the liquid by contacting the donor tissue section and the acceptor material with the liquid at the same time.

2. A diagnostically useful carrier, comprising:
   a solid donor tissue section, and
   an acceptor material comprising an antigen,
   wherein the carrier is configured such that the donor tissue section and the acceptor material comprising an antigen can be co-incubated in a liquid capable of extracting an antibody from said donor tissue section and transporting the antibody to the acceptor material.

3. The carrier according to claim 2, wherein the donor tissue section and the acceptor material comprising an antigen are coated on the surface of the carrier.

4. The carrier according to claim 3, wherein the carrier comprises a first part having a surface coated with the donor tissue section and a second part having a surface coated with the acceptor material,
   wherein the first and the second part are separate and the carrier is configured such that the first and the second part can be contacted to each other via liquid diffusion.

5. The carrier according to claim 3, wherein the donor tissue section and the acceptor material comprising an antigen are on spatially separate biochips.

6. The carrier according to claim 2, wherein a liquid capable of extracting an antibody from said donor tissue section is on the surface of the carrier such that an antibody can be extracted from the donor tissue section and diffuse, via the liquid, to the acceptor material comprising an antigen.

7. The method according to claim 1, wherein the donor tissue section has been obtained from a patient to be diagnosed.

8. The method according to claim 1, wherein the acceptor material comprising an antigen is
   a tissue sample comprising the antigen,
   a cell producing said antigen, or
   an isolated polypeptide.

9. The method according to claim 1, wherein the donor tissue section is a frozen tissue section.

10. The method according to claim 1, wherein
    the disease is a gastroenteropathy,
    the donor tissue section is a gastrointestinal, and
    the antigen is tissue transglutaminase or deamidated gliadin or a variant thereof.

11. The method according to claim 1, wherein the
    disease is pemphigus and/or pemphigoid,
    the donor tissue section is diseased skin tissue, and
    the acceptor material comprises one or more antigens from the group consisting of Dsg1, Dsg3, NC16A, BP180, BP 230, LAMA3, Laminin332, beta4 integrin and collagen type VII and a variant thereof.

12. The method according to claim 1, wherein the disease is Goodpasture syndrome or SLE,
the donor tissue section is diseased kidney tissue, and
the acceptor material comprising the antigen is or is derived from a material selected from the group consisting of antiglomerular basement membrane, dsDNS, human epithelial cells (HEp-2), pLA2R and THSD7A or a variant thereof.

13. The method according to claim 1, wherein
the disease is Crohn's disease,
the donor tissue section is diseased intestinal tissue, and
the acceptor material comprising the antigen is selected from the group consisting of healthy pancreas tissue, CUZD1 and GP2 and a variant thereof.

14. The method according to claim 1, wherein
the disease is myositis,
the donor tissue section is muscle or skin, and
the acceptor material comprising the antigen is MUP-44 or a variant thereof.

15. The carrier according to claim 4, wherein the first and the second part are assembled such that the surface of either the first or the second part faces downwards on the surface of the other one of the first and the second part, such that a drop of liquid may be placed between the surfaces of the first part and the second part to allow diffusion of any antibodies from the donor tissue section to the acceptor material.

16. The method of claim 1, wherein the liquid is an aqueous liquid comprising 0.1 to 10% detergent and having pH 5 to 9.

* * * * *